(12) United States Patent
Dente et al.

(10) Patent No.: US 9,951,303 B2
(45) Date of Patent: Apr. 24, 2018

(54) COMPOSITIONS FOR GRAFTING FRAGRANCE SUBSTANCES

(71) Applicant: Robertet, Inc., Oakland, NJ (US)

(72) Inventors: Stephen V. Dente, Oakland, NJ (US); Ketrin Leka Basile, Oakland, NJ (US); Julianne Harraka, Oakland, NJ (US); Garry Johnson, Oakland, NJ (US); Paul Thottathil, Port Washington, NY (US); Satyabrata Mukherjee, Port Washington, NY (US); Purushothaman Kesavan, Port Washington, NY (US); John Ryan, Port Washington, NY (US)

(73) Assignee: Robertet, Inc., Oakland, NJ (US)

( * ) Notice: Subject to any disclaimer, the term of this patent is extended or adjusted under 35 U.S.C. 154(b) by 215 days.

(21) Appl. No.: 13/793,035

(22) Filed: Mar. 11, 2013

(65) Prior Publication Data
US 2014/0090182 A1 Apr. 3, 2014

Related U.S. Application Data

(60) Provisional application No. 61/708,875, filed on Oct. 2, 2012.

(51) Int. Cl.
| | |
|---|---|
| *C08G 73/10* | (2006.01) |
| *C08F 236/12* | (2006.01) |
| *C08G 63/08* | (2006.01) |
| *D06P 5/08* | (2006.01) |
| *D06M 10/00* | (2006.01) |
| *D06M 13/507* | (2006.01) |
| *C08F 220/06* | (2006.01) |
| *D06M 14/00* | (2006.01) |
| *A61K 8/84* | (2006.01) |
| *A61K 8/85* | (2006.01) |
| *A61K 8/86* | (2006.01) |
| *A61K 8/87* | (2006.01) |
| *A61K 8/891* | (2006.01) |
| *A61K 8/19* | (2006.01) |
| *A61K 8/22* | (2006.01) |
| *A61K 8/23* | (2006.01) |
| *A61Q 15/00* | (2006.01) |
| *A61Q 13/00* | (2006.01) |
| *A61Q 5/02* | (2006.01) |
| *C11D 3/50* | (2006.01) |
| *C08G 65/329* | (2006.01) |
| *C08G 77/00* | (2006.01) |
| *C11D 3/37* | (2006.01) |
| *D06M 13/00* | (2006.01) |
| *D06M 15/643* | (2006.01) |
| *A61K 8/58* | (2006.01) |
| *A61K 8/81* | (2006.01) |
| *C11D 3/16* | (2006.01) |

(52) U.S. Cl.
CPC ............... *C11D 3/505* (2013.01); *A61K 8/19* (2013.01); *A61K 8/22* (2013.01); *A61K 8/23* (2013.01); *A61K 8/585* (2013.01); *A61K 8/8147* (2013.01); *A61K 8/8152* (2013.01); *A61K 8/8194* (2013.01); *A61K 8/84* (2013.01); *A61K 8/85* (2013.01); *A61K 8/86* (2013.01); *A61K 8/87* (2013.01); *A61K 8/891* (2013.01); *A61Q 5/02* (2013.01); *A61Q 13/00* (2013.01); *A61Q 15/00* (2013.01); *C08F 220/06* (2013.01); *C08F 236/12* (2013.01); *C08G 63/08* (2013.01); *C08G 65/329* (2013.01); *C08G 73/10* (2013.01); *C08G 77/00* (2013.01); *C11D 3/162* (2013.01); *C11D 3/373* (2013.01); *C11D 3/3788* (2013.01); *C11D 3/507* (2013.01); *D06M 10/00* (2013.01); *D06M 13/005* (2013.01); *D06M 13/507* (2013.01); *D06M 14/00* (2013.01); *D06M 15/643* (2013.01); *D06P 5/08* (2013.01); *A61K 2800/57* (2013.01)

(58) Field of Classification Search
CPC ...... G08G 65/329; G08G 77/00; C11D 3/505; C11D 3/373; C11D 3/3788; C11D 3/162; C11D 3/507; C08G 73/10; C08G 63/08; C08F 236/12; A61K 8/8147; A61K 8/8152; A61K 8/8194; A61K 8/84; A61K 8/85; A61K 8/86; A61K 8/87; A61K 8/891; A61K 8/19; A61K 8/22; A61K 8/23; A61K 8/585; A61K 2800/57; A61Q 15/00; A61Q 13/00; A61Q 5/02; D06M 14/00; D06M 15/643; D06M 10/00; D06M 13/005; D06M 13/507; D06P 5/08
See application file for complete search history.

(56) References Cited

U.S. PATENT DOCUMENTS 2,348,552 A * 5/1944 Little .................... D06M 15/17
106/147.5
3,868,433 A * 2/1975 Bartz et al. ..................... 525/78
(Continued)

FOREIGN PATENT DOCUMENTS

EP 2 267 217 12/2010

OTHER PUBLICATIONS

International Search Report and Written Opinion dated Jan. 29, 2014 in corresponding International Application No. PCT/US2013/056479.

(Continued)

*Primary Examiner* — Amina Khan
(74) *Attorney, Agent, or Firm* — Norris McLaughlin & Marcus PA

(57) ABSTRACT

This disclosure relates to composition for grafting fragrance substances, as well as related articles, consumer products, and methods.

31 Claims, 8 Drawing Sheets

(56) References Cited

U.S. PATENT DOCUMENTS

| | | | |
|---|---|---|---|
| 4,552,777 | A | 11/1985 | Dente et al. |
| 5,407,728 | A * | 4/1995 | Kerr et al. ................. 428/195.1 |
| 5,486,210 | A | 1/1996 | Kerr et al. |
| 6,180,039 | B1 | 1/2001 | Sanduja et al. |
| 6,638,319 | B2 | 10/2003 | Sanduja et al. |
| 6,783,865 | B2 | 10/2004 | Sanduja et al. |
| 6,908,976 | B2 | 6/2005 | Sanduja et al. |
| 6,994,794 | B2 | 2/2006 | Hansen et al. |
| 7,309,745 | B2 | 12/2007 | Sanduja et al. |
| 7,413,744 | B2 | 8/2008 | Ichinohe |
| 7,723,285 | B2 | 5/2010 | Bruza et al. |
| 7,998,279 | B2 | 8/2011 | Schutz et al. |
| 8,124,114 | B2 | 2/2012 | Dente et al. |
| 2003/0046770 | A1 * | 3/2003 | Sanduja et al. .............. 8/115.51 |
| 2003/0079296 | A1 | 5/2003 | Sanduja et al. |
| 2005/0095266 | A1 * | 5/2005 | Perichaud et al. ............ 424/423 |
| 2006/0018977 | A1 | 1/2006 | Bruza et al. |
| 2010/0143681 | A1 * | 6/2010 | Yano .................... B32B 17/067 428/216 |

OTHER PUBLICATIONS

Chrusciel, J.A. "Modification of Thermoplastics with Reactive Silanes and Siloxanes", Technical University of Lódź, Faculty of Chemistry, Institute of Polymer and Dye Technology, pp. 156-192.
Dr. A. Bhattacharya, et al., "Polymer Grating and Crosslinking", a John Wiley & Sons, Inc. Publication, pp. 1-343.

* cited by examiner

(12) United States Patent
US 9,951,303 B2

COMPOSITIONS FOR GRAFTING FRAGRANCE SUBSTANCES

CROSS-REFERENCE TO RELATED APPLICATION

This application claims priority to U.S. Provisional Application No. 61/708,875, filed on Oct. 2, 2012, the contents of which are hereby incorporated by reference in their entirety.

TECHNICAL FIELD

This disclosure relates to composition for grafting fragrance substances, as well as related articles, consumer products, and methods.

BACKGROUND

Many scented products (e.g. household or personal care products) are known to provide a pleasant smelling fragrance. However, the difficulty to develop a scented product with longevity when applied to different materials (e.g., clothing, countertops, carpet, hair or skin) has been dependent on the solubility and/or volatility of some fragrances.

SUMMARY

This disclosure is based on the unexpected discovery that certain graft compositions (e.g., those containing at least a fragrance, at least a coupling agent, at least a polymerizable prepolymer, at least a graft initiator, and at least a catalyst) can be included in a product (e.g. hair spray, a carpet cleaner, or a laundry product) to maintain a pleasant smell over a long period of time to a surface (e.g. fabric, countertops, hair or skin) after subjecting the surface to a cleaning and/or moisturizing treatment.

In one aspect, this disclosure features a composition that includes a fragrance, a coupling agent, a polymerizable prepolymer, a graft initiator; and a catalyst.

In another aspect, this disclosure features a consumer product that includes the composition mentioned above or a reaction product of the composition mentioned above.

In another aspect, this disclosure features a method of washing a cloth item. The method includes applying the composition mentioned above to the cloth item, and washing the cloth item.

In still another aspect, this disclosure features an article that includes a substrate having a surface and a compound bonded to the surface. The compound contains a polymeric moiety and a fragrance moiety bonded to the polymeric moiety.

Embodiments can include one or more of the following features.

In some embodiments, the coupling agent can be a silane of formula (I):

Si—$R_1R_2R_3R_4$ (I), in which $R_1$ is $C_2$-$C_{10}$ alkenyl (e.g., vinyl), and each of $R_2$, $R_3$, and $R_4$, independently, is $C_1$-$C_{10}$ alkyl, $C_1$-$C_{10}$ alkoxy (e.g., methoxy), or $C_6$-$C_{30}$ aryl.

In some embodiments, the composition can include from 0.0001 wt % to 0.5 wt % of the coupling agent.

In some embodiments, the polymerizable prepolymer can include a polyalkylene prepolymer, a urethane prepolymer, an acrylic prepolymer, an epoxy prepolymer, a bisphenol A prepolymer, a silicone prepolymer, a polyester prepolymer, a polyalkylene glycol prepolymer, a polycarbodiimide prepolymer, a polydiene prepolymer or a phenolic prepolymer.

In some embodiments, the composition can include from 2 wt % to 50 wt % of the prepolymer.

In some embodiments, the graft initiator can include a salt of Ag, Fe, Co, or Cu, or a mixture thereof. For example, the graft initiator can include silver perchlorate. In some embodiments, the composition can include from 0.01 ppm to 10 ppm of the graft initiator.

In some embodiments, the catalyst can include a peroxide (e.g., urea peroxide), a peracid, a perbenzoate, a metabisulfite, a persulfate, or a mixture thereof. In some embodiments, the composition can include from 0.01 ppm to 10 ppm of the catalyst.

In some embodiments, the composition can further include a surfactant, such as a non-ionic surfactant. For example, the surfactant can include a polyalkylene glycol. In some embodiments, the composition can include from 0.01 wt % to 0.5 wt % of the surfactant.

In some embodiments, the composition can include from 1 wt % to 80 wt % of the fragrance.

In some embodiments, the composition can further include a solvent. For example, the solvent can include a mineral oil, an alkene, an ether, an ester, or a mixture thereof. In some embodiments, the composition can include from 10 wt % to 80 wt % of the solvent.

In some embodiments, the composition can include at least one fragrance, at least two prepolymers, at least two coupling agents, at least one graft initiator, at least one catalyst, at least one surfactant, and at least three solvents. For example, the composition can include the fragrance, an isobutylene/butylene copolymer, a hydrogenated rosin ester, benzyl benzoate, a terpene, a mineral oil, a non-ionic surfactant, trimethoxyvinylsilane, a polyalkylene glycol, an organomodified polydimethylsiloxane, urea peroxide, and silver perchlorate.

In some embodiments, the composition can include from 1 wt % to 80 wt % of the fragrance, from 0.0001 wt % to 0.5 wt % of the coupling agent, from 2 wt % to 50 wt % of the prepolymer, from 0.01 ppm to 10 ppm of the graft initiator, and from 0.01 ppm to 10 ppm of the catalyst. In some embodiments, the above-mentioned composition can further include from 0.01 wt % to 0.5 wt % of the surfactant and from 10 wt % to 80 wt % of the solvent.

In some embodiments, the product can be a detergent, a softener, a deodorant, a shampoo, a fabric refresher, a dryer sheet, or a surface cleaner.

In some embodiments, the method can further include drying the cloth item after the washing step.

In some embodiments, the polymeric moiety can include a polybutylene, a polyurethane, an acrylic polymer, an epoxy polymer, a bisphenol A-based polymer, a silicone polymer, or a phenolic polymer.

In some embodiments, the fragrance moiety can be covalently bonded to the polymeric moiety (e.g., through a silane moiety).

In some embodiments, the compound can be covalently bonded to the surface of the substrate (e.g., through a siloxane moiety).

In some embodiments, the article can be a cloth item.

Other features, objects, and advantages of the subject matter disclosed herein are apparent from the description, drawings, and claims.

DESCRIPTION OF DRAWINGS

Like reference symbols in the various drawings indicate like elements.

DETAILED DESCRIPTION

Figure 1:
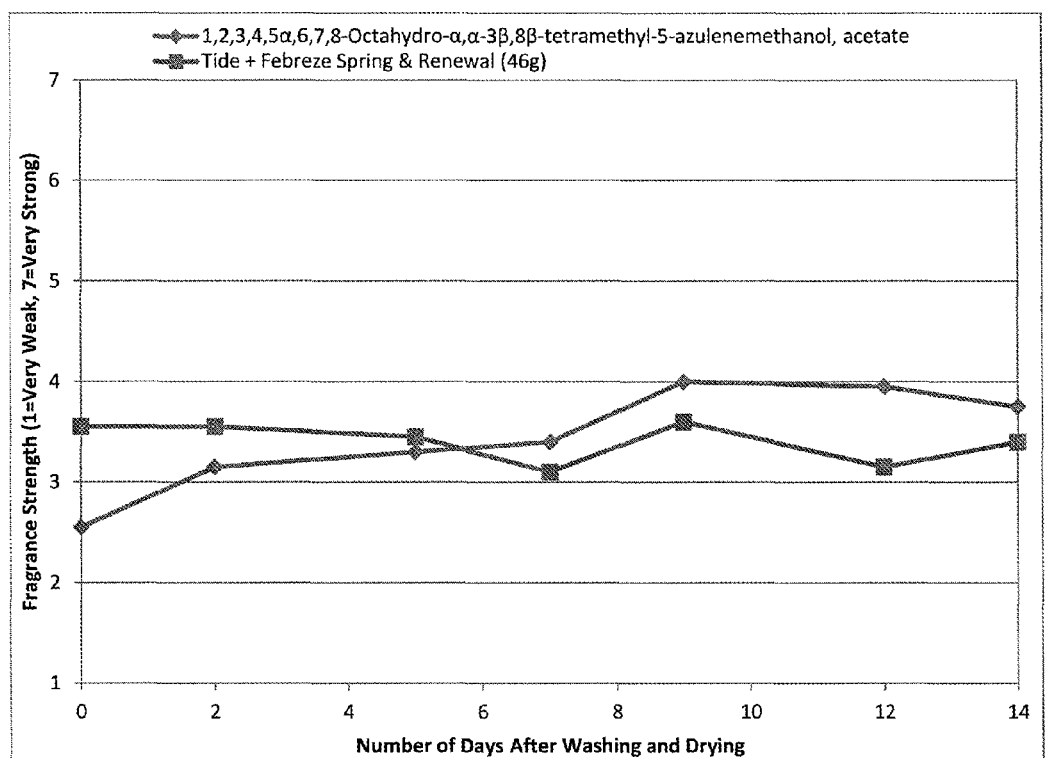
FIG. 1 is a graph comparing the fragrance strength and duration between a LLD control sample and a LLD test sample containing Formula 28 and guaiol acetate (also known as 1,2,3,4,5α,6,7,8-octahydro-α,α-3β,8β-tetramethyl-5-azulenemethanol, acetate).

This disclosure generally relates to grafting compositions for attaching (e.g., bonding or grafting) fragrances to a surface of an article (e.g., a cloth item, furniture, or floor).

In some embodiments, this disclosure features grafting compositions that include at least one fragrance, at least one coupling agent, at least one polymerizable prepolymer, at least one graft initiator, and at least one catalyst. For example, the grafting compositions can include two or more (e.g., three or four) of each of the above ingredients.

In general, the coupling agent mentioned herein refers to an agent capable of at least binding (e.g., through chemical bonding) the prepolymer with the fragrance to form a fragrance-containing prepolymer. In some embodiments, the coupling agent can also bind (e.g., through chemical bonding) the prepolymer or the fragrance-containing prepolymer to a surface of an article (e.g, a cloth item, furniture, or floor).

In some embodiments, the coupling agent can be a multifunctional silane. For example, the multifunction silane can be a silane of formula (I):

Si—R$_1$R$_2$R$_3$R$_4$ (I), in which R$_1$ can be C$_1$-C$_{10}$ alkyl (e.g., methyl or ethyl) or C$_2$-C$_{10}$ alkenyl (e.g., vinyl, methylvinyl, or allyl), and each of R$_2$, R$_3$, and R$_4$, independently, can be C$_1$-C$_{10}$ alkyl, C$_1$-C$_{10}$ alkoxy (e.g., methoxy, ethoxy, n-propoxy, or iso-propoxy), or C$_6$-C$_{30}$ aryl (e.g., phenyl). Commercially available examples of multifunctional silane include SILQUEST A-171 silane (i.e., vinyltrimethoxysilane) available from Momentive Performance Materials (Friendly, W. Va.) or COATOSIL 1770 (i.e., β-(3,4-epoxycyclohexyl ethyltriethoxysilane) available from Momentive Performance Materials (Friendly, W. Va.).

The term "alkyl" mentioned herein refers to a saturated, linear or branched hydrocarbon moiety, such as —CH$_3$ or —CH(CH$_3$)$_2$. The term "alkenyl" mentioned herein refers to a linear or branched hydrocarbon moiety that contains at least one double bond, such as —CH=CH—CH$_3$ or —CH$_2$—CH=CH$_2$. The term "aryl" mentioned herein refers to a hydrocarbon moiety having one or more aromatic rings. Examples of aryl moieties include phenyl (Ph), phenylene, naphthyl, naphthylene, pyrenyl, anthryl, and phenanthryl.

Alkyl, alkenyl, alkoxy, and aryl mentioned herein include both substituted and unsubstituted moieties, unless specified otherwise. Possible substituents include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl (e.g., epoxy), C$_1$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, C$_1$-C$_{20}$ dialkylamino, arylamino, diarylamino, C$_1$-C$_{10}$ alkylsulfonamino, arylsulfonamino, C$_1$-C$_{10}$ alkylimino, arylimino, C$_1$-C$_{10}$ alkylsulfonimino, arylsulfonimino, hydroxyl, halo, thio, C$_1$-C$_{10}$ alkylthio, arylthio, C$_1$-C$_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester.

In some embodiments, the coupling agent can be a multifunctional polysiloxane, such as a polysiloxane containing two or more reactive groups (e.g., epoxy groups or hydroxyl groups). A commercially available example of a multifunctional polysiloxane is COATOSIL 3501 available from Momentive Performance Materials (Friendly, W. Va.).

In some embodiments, the grafting compositions disclosed herein include at least 0.1 ppm (e.g., at least 0.5 ppm, at least 1 ppm, at least 5 ppm, at least 10 ppm, at least 50 ppm, at least 100 ppm, or at least 500 ppm) and/or at most 5000 ppm (e.g., at most 2500 ppm, at most 1000 ppm, at most 750 ppm, or at most 500 ppm) of the coupling agent. Without wishing to be bound by theory, it is believed that adding too much of the coupling agent (e.g., more than about 5000 ppm) to a grafting composition described herein would not necessarily maintain the fragrance on an article longer, and adding too little of the coupling agent (e.g., less than about 0.1 ppm) would not effectively attach the fragrance to an article.

Without wishing to be bound by theory, it is believed that, after a grafting composition is formed, the coupling agent can attach the fragrance to the prepolymer at ambient conditions or at an elevated temperature (e.g., from 30° C. to 80° C.) to form a fragrance-containing prepolymer before the grafting composition is used (e.g., mixed with a laundry product to wash a cloth item). Further, without wishing to be bound by theory, it is believed that the fragrance-containing prepolymer can be polymerized through a radical polymerization at the ambient conditions or at an elevated temperature (e.g., from 30° C. to 80° C.) to form a fragrance-containing polymer, which can be attached to an article (e.g., a cloth item when a laundry product containing the graft composition is used to wash a cloth item). Alternatively, without wishing to be bound by theory, it is believed that the prepolymer or fragrance-containing prepolymer can first be attached to an article (e.g., a cloth item) and then form a polymer through a radical polymerization.

In some embodiments, the grafting compositions disclosed herein can include two or more (e.g., three or four) coupling agents. Without wishing to be bound by theory, it is believed that including two or more coupling agents in a grafting composition can significantly enhance the composition's efficacy in grafting the fragrance-containing polymer onto an article (e.g., a cloth item).

In general, the term "prepolymer" refers to a material capable of undergoing polymerization to form a polymer having a molecular weight higher than that of the material before polymerization. In some embodiments, the prepolymer can be a pre-formed polymer having reacting groups and being capable of further polymerization to form a polymer of a higher molecular weight. Examples of such prepolymers include a polyalkylene prepolymer (e.g., a polyethylene, polypropylene, or polybutylene prepolymer), a urethane prepolymer, an acrylic prepolymer, an epoxy prepolymer, a bisphenol A prepolymer, a silicone prepolymer, a polyester prepolymer, a polyalkylene glycol prepolymer (e.g., a polyethylene glycol or a polypropylene glycol), a polycarbodiimide prepolymer, a polydiene prepolymer (a polybutadiene prepolymer), or a phenolic prepolymer. The prepolymers mentioned herein can also include a copolymer of the exemplary prepolymers described above. Commercially available prepolymers include INDOPOL H100 (i.e., a polybutylene prepolymer) available from Amoco Chemical Company (Chicago, Ill.), SOREZ 100 (i.e., a polyethylene glycol polyester) available from International Specialty Products (Wayne, N.J.), STABAXOL 122P (i.e., a polycarbodiimide prepolymer) available from Rhein Chemie Corporation (Trenton, N.J.), KRASOL LBH 3000 (i.e., a hydroxyl-terminated polybutadiene) available from Sartomer Company, Inc., (Exton, Pa.), CAPA 2403D (i.e., a polyester diol formed from caprolactone and 1,4-butanediol) available from Perstorp Polyols, Inc., Dow Corning EL8050 (i.e., a silicone elastomer) available from Dow Corning (Midland, Mich.), TEGO GLIDE 450 (i.e., a polyether modified polysiloxane) available from Evonik Degussa Corporation (Parsippany, N.J.), TEGO PROTECT 5000 (i.e., a hydroxy alkyl polydimethylsiloxane) available from Evonik Degussa Corporation (Parsippany, N.J.), HYCAR 1300X-21 (i.e., a butadiene-acrylonitrile copolymer) available from Lubrizol Advanced Materials, Inc. (Cleveland, Ohio), and CARBOPOL 941 (i.e., a polyacrylic acid) available from Lubrizol Advanced Materials, Inc. (Cleveland, Ohio).

In some embodiments, a prepolymer mentioned herein can be a polymerizable monomer or oligomer. Suitable examples of such prepolymers include acrylonitrile, sodium vinyl sulfonate, an ester, an alkylpyrrolidone, a carbodiimide, or a mixture thereof. Commercially available examples of polymerizable monomers include HERCOLYN D (i.e., a methyl ester of hydrogenated rosin) available from Pinova, Inc. (Brunswick, Ga.), TECKROS RL 5 (i.e., rosin esters) available from Teckrez Inc. (Fleming Island, Fla.), MICROFLEX 1 (i.e., alkylpyrrolidones) available from International Specialty Products (Wayne, N.J.), SURFADONE LP 300 (i.e., 1-dodecyl-2-pyrrolidinone) available from International Specialty Products (Wayne, N.J.), SURFADONE LP 100 (i.e., caprylyl pyrrolidone) available from International Specialty Products (Wayne, N.J.), and STABAXOL I (containing 2,2',6,6'-tetraisopropyldiphenyl carbodiimide) available from Rhein Chemie Corporation (Trenton, N.J.).

In some embodiments, the grafting compositions disclosed herein can include at least 2 wt % (e.g., at least 5 wt %, at least 10 wt %, at least 15 wt %, at least 20 wt %, at least 25 wt %, or at least 30 wt %) and/or at most 50 wt % (e.g., at most 45 wt %, at most 40 wt %, at most 35 wt %, at most 30 wt %, or at most 25 wt %) of a prepolymer.

Without wish to be bound by theory, it is believed that, during use of the grafting compositions disclosed herein, the polymerizable prepolymer disclosed herein can be attached to a fragrance at one end and attached to an article (e.g., a cloth item) at the other end (e.g., through a polymerization reaction). As a result, the fragrance can be attached to the article and maintained on the article even after washing and/or drying, and can be gradually released over a long period of time (e.g., up to 14 days or more), thereby giving a consumer perceived freshness of the article.

In some embodiments, the grafting compositions disclosed herein can include two or more (e.g., three or four) polymerizable prepolymers. Without wishing to be bound by theory, it is believed that including two or more polymerizable prepolymers in a grafting composition can significantly enhance the composition's efficacy in grafting the fragrance onto an article (e.g., a cloth item).

In some embodiments, the graft initiator disclosed herein can include a salt of Ag, Fe, Co, or Cu, or a mixture thereof. For example, the graft initiator can include a metal ion selected from $Ag^+$, $Fe^{2+}$, $Fe^{3+}$, $Co^{2+}$, and $Cu^{2+}$. For example, the graft initiator can be silver perchlorate (i.e., $AgClO_4$) or ferrous ammonium sulfate (i.e., $(NH_4)_2Fe(SO_4)_2$).

In general, the graft initiator can be present in the grafting compositions disclosed herein in any suitable amount. In some embodiments, the grafting compositions can include at least 0.01 ppm (e.g., at least 0.05 ppm, at least 0.1 ppm, or at least 0.5 ppm) and/or at most 10 ppm (e.g., at most 7.5 ppm, at most 5 ppm, at most 2.5 ppm, or at most 1 ppm) of the graft initiator.

Without wishing to be bound by theory, it is believed that the graft initiator can activate (e.g., by abstracting a hydrogen or a radical) the surface of an article (e.g., a cloth item, furniture, or floor) and starts polymerizing the prepolymer (with or without a fragrance attached to it) to form a polymer attached to the surface. When the prepolymer is bonded with a fragrance, the above process can result in a fragrance attached to the surface, which can be gradually released over a long period of time. Typically, when the above process is completed, the graft initiator is consumed.

In some embodiments, the catalyst disclosed herein can include a peroxide, a peracid (e.g., peracetic acid), a perbenzoate (e.g., tert-butyl perbenzoate), a metabisulfite (e.g., sodium metabisulfite), a persulfate (e.g., ammonium persulfate), or a mixture thereof. Exemplary peroxides include methylethyl ketone peroxide, urea peroxide, hydrogen peroxide, tert-butylhydroperoxide, ditert-butyl peroxide, benzoyl peroxide, dicumyl peroxide, or lauryl peroxide.

In general, the catalyst can be present in the grafting compositions disclosed herein in any suitable amount. In some embodiments, the grafting compositions can include at least 0.01 ppm (e.g., at least 0.05 ppm, at least 0.1 ppm, or at least 0.5 ppm) and/or at most 10 ppm (e.g., at most 7.5 ppm, at most 5 ppm, at most 2.5 ppm, or at most 1 ppm) of the catalyst.

Without wishing to be bound by theory, it is believed that the catalyst can activate the graft initiator, facilitate polymerization, and/or transforms a used graft initiator into an entity capable of initiating another graft site on the surface of an article.

In general, the grafting compositions disclosed herein include at least one (e.g., two, three, or four) fragrance that can be attached to the surface of an article (e.g., a cloth item, furniture, or floor). As used herein, the term "fragrance" refers to a compound or compounds that possess a scent or aroma. Exemplary fragrances include esters, aldehydes, ethers, nitriles, ketones, or alcohols. Examples of esters include methyl 2-aminobenzoate, 2-(4-methylcyclohexyl) propan-2-yl acetate, ethyl 2-methylbutanoate, or guaiol acetate. Examples of aldehydes include benzaldehyde, 1-methyl-4-(4-methylpentyl)cyclohex-3-ene-1-carbaldehyde, 4-propan-2-ylbenzaldehyde, 3-(4-propan-2-ylphenyl) butanal, 1,3-benzodioxole-5-carbaldehyde, 3-(4-tert-butylphenyl)butanal, 2,4-dimethylcyclohex-3-ene-1-carbaldehyde, 1,1-dimethoxypropan-2-ylbenzene, dodec-3-enal, n-dodecanal, 3-(3-propan-2-ylphenyl)butanal, 2-benzylideneheptanal, 3-phenylprop-2-enal, 3-(1,3-benzodioxol-5-yl)-2-methylpropanal, 3-(4-methoxyphenyl)-2-methylpropanal, 2-phenylpropanal, 2-phenylacetaldehyde, 4-(4-hydroxy-4-methylpentyl)-3-cyclohexene-1-carboxaldehyde, 2-(phenylmethylidene)octanal, 4-methoxybenzaldehyde, or 2,6-dimethylhept-5-enal. An example of an ether is 2,4-dimethyl-4,4-a,5,9b-tetrahydroindeno[1,2-d][1,3]dioxine. An example of a nitrile is 3,7-dimethyloct-6-enenitrile. Examples of ketones include (E)-4-(2,6,6-trimethyl-1-cyclohex-2-enyl)but-3-en-2-one, methyl cedryl ketone (also known as 1-(2,3,4,7,8,8a-hexahydro-3,6,8,8-tetramethyl-1H-ethanone), or (E)-4-(2,6,6-trimethyl-1-cyclohexenyl)but-3-en-2-one. Examples of alcohols include 3,7-dimethyl-1,7-octane diol, (Z)-3-methyl-5-(2,2,3-trimethyl-1-cyclopent-3-enyl)pent-4-en-2-ol, 2-(4-methyl-1-cyclohex-3-enyl)propan-2-ol, 3,7-dimethylocta-1,6-dien-3-ol, or hexan-1-ol. In some embodiments, the grafting composition can include at least 1 wt % (e.g., at least 5 wt %, at least 10 wt %, at least 15 wt %, at least 20 wt %, at least 25 wt %, or at least 30 wt %) and/or at most 80 wt % (e.g., at most 75 wt %, at most 70 wt %, at most 65 wt %, at most 60 wt %, at most 55 wt %, or at most 50 wt %) of the fragrance. In some embodiments, the grafting compositions can include a mixture of fragrances. In such embodiments, without wishing to be bound by theory, it is believed that at least one fragrance in the mixture can be attached to the prepolymer, which can subsequently be attached to an article. In some embodiments, the grafting compositions can include two or more fragrances (e.g., a fragrance containing a carbonyl group and a fragrance containing an amine) that are capable of forming a Schiff base. Without wishing to be bound by theory, it is believed that such a grafting composition can be grafted onto an article relatively easily.

In some embodiments, the grafting compositions disclosed herein can include at least one (e.g., two, three, or four) surfactant, such as a non-ionic surfactant, an anionic surfactant, a cationic surfactant, or an amphoteric surfactant. An example of a suitable non-ionic surfactant is a polyalkylene glycol (e.g., polyethylene glycol (PEG) or a polypropylene glycol (PPG)) or a copolymer thereof (e.g., a PEG-PPG copolymer). Commercially available examples of non-ionic surfactants include ECOSURF SA-7 (i.e., a mixture including C6-C12 ethoxylated propoxylated alcohol, C10-C16 ethoxylated propoxylated alcohol, and polyethylene oxide), PLURONIC F-64 (i.e., a PEG-PPG copolymer), PLURONIC F-127 (i.e., a PEG-PPG copolymer), TRITON X-100 (i.e., a polyethylene glycol octylphenyl ether), PLURACOL WS 2000 (i.e., a polyalkylene glycol derivative) available from BASF Corporation (Florham Park, N.J.), and IGEPAL CO-630 (polyoxyethylene nonylphenylether). A commercially available example of a cationic surfactant is CRODAQUAT 1207 (i.e., a quaternary polyoxyethyene alkylamine) available from Croda Inc. (Edison, N.J.). In some embodiments, the grafting compositions can include at least 0.01 wt % (e.g., at least 0.025 wt %, at least 0.05 wt %, at least 0.075 wt %, at least 0.1 wt %, at least 0.15 wt %, or at least 0.2 wt %) and/or at most 0.5 wt % (e.g., at most 0.45 wt %, at most 0.4 wt %, at most 0.35 wt %, at most 0.3 wt %, or at most 0.25 wt %) of the surfactant. Without wishing to be bound by theory, it is believed that the surfactant in a grafting composition can facilitate dispersion of organic components (e.g., fragrance, pre-polymer and/or fragrance-containing prepolymer or polymer) in water when the grafting composition is used (e.g., to wash clothes).

In some embodiments, the grafting compositions disclosed herein can include at least one (e.g., two, three, or four) solvent (e.g., an aqueous solvent or an organic solvent). Exemplary organic solvents include a mineral oil, an alkene, an ether, and an ester (e.g., diethyl phthalate). Exemplary aqueous solvents include water and a mixture of water and one or more other solvents (e.g., an alcohol). Commercially available examples of solvents include CITROFLEX A-4 (i.e., acetyl tributyl citrate) available from Vertellus Performance Materials Inc. (Greensboro, N.C.), DRAKEOL 7LT (i.e., a mineral oil) available from Calumet Specialty Products Partners, L.P. (Indianapolis, Ind.), and DOWANOL PnP (i.e., dipropylene glycol n-propyl ether) available from The Dow Chemical Company (Midland, Mich.). In some embodiments, the grafting compositions can include at least 10 wt % (e.g., at least 15 wt %, at least 20 wt %, at least 25 wt %, at least 30 wt %, at least 35 wt %, or at least 40 wt %) and/or at most 80 wt % (e.g., at most 75 wt %, at most 70 wt %, at most 65 wt %, at most 60 wt %, at most 55 wt %, or at most 50 wt %) of the solvent.

In some embodiments, the grafting compositions disclosed herein can include one or more additives. For example, the grafting compositions can include a moisture scavenger to absorb any moisture in the compositions. A commercially available example of a moisture scavenger is Borchi Nox M2 available from OMG Borchers GmbH (Langenfeld, Germany). As another example, the grafting compositions can include an antioxidant minimize oxidation of the compositions and/or an anti-static agent to minimize formation of static charges in the compositions. A commercially available example of an antioxidant is IRGANOX 1010 (i.e., pentaerythritol tetrakis(3-(3,5-di-tert-butyl-4-hydroxyphenyl)propionate) available from Ciba Specialty Chemicals. A commercially available example of an anti-static agent is ARQUAD 2HT 75 (mainly dimethyldioctadecylammonium chloride) available from Sigma-Aldrich (St. Louis, Mo.).

Without wishing to be bound by theory, it is believed that, during use, the grafting compositions disclosed herein can undergo the following reactions to attach a polymer (e.g., a polymer containing a fragrance) to a surface of an article. In the following reactions, "S" stands for a substrate (e.g., an article described herein), "GI" stands for a graft initiator, "ROOH" stands for a peroxide, "P" stands for a prepolymer or a prepolymer containing a fragrance, and "*" stands for a radical. Specifically, the initiation reactions for the grafting process can occur as shown in reactions (1) and (2) below to produce activated graft initiator:

$$ROOH \rightarrow RO^* + {}^*OH \quad (1)$$

$$RO^* + GI \rightarrow RO + GI^* \quad (2)$$

The activated graft initiator can then activate the substrate to allow it to attach a polymer to a surface of the substrate, as shown in reactions (3)-(5) below:

$$S-H + GI^* \rightarrow S^* + GI \quad (3)$$

$$S^* + P \rightarrow S-P^* \quad (4)$$

$$S-P^* + P \rightarrow S-P-P^* \quad (5)$$

In some embodiments, the activated graft initiator can activate the prepolymer to attach it to a surface of the substrate, as shown in reactions (6)-(8) below:

$$P + GI^* \rightarrow P^* + GI \quad (6)$$

$$S + P^* \rightarrow S-P^* \quad (7)$$

$$S-P^* + P \rightarrow S-P-P^* \quad (8)$$

In some embodiments, the activated graft initiator can activate the prepolymer to form a polymer, which can then be attached to the substrate, as shown in reactions (9)-(11) below.

$$P + GI^* \rightarrow P^* + GI \quad (9)$$

$$P + P^* \rightarrow P—P^* \quad (10)$$

$$S + P—P^* \rightarrow S—P—P^* \quad (11)$$

The species S—P—P* can undergo further chain propagation until chain termination occurs (e.g., by radical combination), as shown in reactions (12)-(14) below:

$$S—P—P^* + RO^* \rightarrow S—P—P—OR \quad (12)$$

$$S—P—P^* + S—P^* \rightarrow S—P—P—P—S \quad (13)$$

$$S—P—P^* + S—P—P^* \rightarrow S—P—P—P—P—S \quad (14)$$

In general, the grafting compositions disclosed herein can be prepared by methods known in the art. For example, a grafting composition can be formed by mixing all of the ingredients together. As another example, a grafting composition can be formed by first mixing all of the ingredients except for the fragrance. The mixture thus formed can be allowed to stand for a certain period of time (e.g., 24 hours). The fragrance can then be added to the mixture to form the grafting composition. In some embodiments, the grafting composition thus formed is allowed to stand for a certain period of time (e.g., 24 hours) before use or incorporated into a consumer product.

In some embodiments, the grafting compositions disclosed herein can be incorporated into a consumer product, such as a detergent, a softener, a deodorant, a shampoo, a fabric refresher, a dryer sheet, or a surface cleaner. The consumer product can be formed by adding a grafting composition to an existing product (e.g., a detergent) at a suitable amount. In some embodiments, a consumer product can include at least 0.1 wt % (e.g., at least 0.2 wt %, at least 0.4 wt %, at least 0.6 wt %, at least 0.8 wt %, at least 1 wt %, or at least 2 wt %) and/or at most 5 wt % (e.g., at most 4.5 wt %, at most 4 wt %, at most 3.5 wt %, at most 3 wt %, at most 2.5 wt %, or at most 2 wt %) of a grafting composition.

This disclosure also features a method of using the grafting compositions disclosed herein. For example, the disclosure features a method of washing a cloth item that includes applying a grafting composition (e.g., incorporated in a consumer product such as a detergent or a softener) to the cloth item, and washing the cloth item. Without wishing to be bound by theory, it is believed that the fragrance in the grafting composition can be attached to the cloth item and maintained on the cloth item even after washing and/or drying. In addition, the fragrance can be gradually released from the cloth item over a long period of time (e.g., up to 14 days or more), thereby giving a consumer perceived freshness of the cloth item.

In some embodiments, this disclosure features an article that includes a substrate having a surface and a compound bonded (e.g., covalently bonded) to the surface. Exemplary articles include a cloth item, furniture, and floor. The substrate can be formed from a suitable polymer, such as cellulose, a nylon, a polypropylene, or a polyester. The compound can include a polymeric moiety and a fragrance moiety bonded (e.g., covalently bonded) to the polymeric moiety. The polymeric moiety and the fragrance moiety can be obtained from the prepolymer and fragrance described above, respectively. In some embodiments, the fragrance moiety is covalently bonded to the polymeric moiety through a silane moiety, which can be derived from the multifunctional silane described above. In some embodiments, the compound is covalently bonded to the surface through a siloxane moiety.

The contents of all publications cited herein (e.g., patents, patent application publications, and articles) are hereby incorporated by reference in their entirety.

The following examples are illustrative and not intended to be limiting.

Example 1: Preparation of Formula 1

Formula 1 was prepared by mixing together the Ingredients listed in the following table.

| Ingredients | Amount (parts by weight) |
|---|---|
| CITROFLEX A-4 (Acetyl Tributyl Citrate) | 45 |
| Diethyl Phthalate | 45 |
| MICROFLEX 1 (Alkylpyrrolidones) | 5 |
| SOREZ 100 (Polyethylene Glycol Polyester) | 2 |
| STABAXOL 122P (Polycarbodiimide) | 10 |
| Silane A171 (Vinyltrimethoxysilane) | 0.1 |
| Benzoyl Peroxide (0.1 wt % in Diethyl Phthalate) | 0.01 |
| Silver Perchlorate (0.1 wt % in Ethanol) | 0.01 |

Example 2: Preparation of Formula 2

Formula 2 was prepared by mixing together the Ingredients listed in the following table.

| Ingredients | Amount (parts by weight) |
|---|---|
| CITROFLEX A-4 (Acetyl Tributyl Citrate) | 45 |
| Diethyl Phthalate | 45 |
| CRODAQUAT 1207 (a cationic surfactant) | 2 |
| HERCOLYN D (Methyl Ester of Hydrogenated Rosin) | 5 |

-continued

| Ingredients | Amount (parts by weight) |
| --- | --- |
| TRITON X-100 (Polyethylene Glycol Octylphenyl Ether) | 1 |
| Silane A171 (Vinyltrimethoxysilane) | 0.2 |
| HYCAR 1300X-21 (Butadiene-Acrylonitrile Copolymer) | 3 |
| COATOSIL 3501 (Organomodified Polydimethylsiloxane) | 0.1 |
| Benzoyl Peroxide (0.1 wt % in Diethyl Phthalate) | 0.1 |
| Silver Perchlorate (0.1 wt % in Ethanol) | 0.1 |

Example 3: Preparation of Formula 3

Formula 3 was prepared by mixing together the Ingredients listed in the following table.

| Ingredients | Amount (parts by weight) |
| --- | --- |
| CITROFLEX A-4 (Acetyl Tributyl Citrate) | 45 |
| Diethyl Phthalate | 45 |
| CRODAQUAT 1207 (a cationic surfactant) | 2 |
| HERCOLYN D (Methyl Ester of Hydrogenated Rosin) | 3 |
| STABAXOL 122P (Polycarbodiimide) | 2 |
| HYCAR 1300X-21 (Butadiene-Acrylonitrile Copolymer) | 2 |
| TRITON X-100 (Polyethylene Glycol Octylphenyl Ether) | 1 |
| Silane A171 (Vinyltrimethoxysilane) | 0.2 |
| COATOSIL 1770 (β-(3,4-epoxycyclohexyl) ethyltriethoxysilane) | 0.1 |
| Benzoyl Peroxide (0.1 wt % in Diethyl Phthalate) | 0.1 |
| Silver Perchlorate (0.1 wt % in Diethyl Phthalate) | 0.1 |

Example 4: Preparation of Formula 4

Formula 4 was prepared by mixing together the Ingredients listed in the following table.

| Ingredients | Amount (parts by weight) |
| --- | --- |
| CITROFLEX A-4 (Acetyl Tributyl Citrate) | 45 |
| Diethyl Phthalate | 45 |
| STABAXOL 122P (Polycarbodiimide) | 3 |
| TECKROS RL 5 (Rosin Esters) | 2 |
| HERCOLYN D (Methyl Ester of Hydrogenated Rosin) | 2 |
| TRITON X-100 (Polyethylene Glycol Octylphenyl Ether) | 0.2 |
| KRASOL LBH 3000 (Hydroxy-terminated Polybutadiene) | 2 |
| Silane A171 (Vinyltrimethoxysilane) | 0.1 |
| Benzoyl Peroxide (in Diethyl Phthalate) | 0.1 |
| Silver Perchlorate (0.1 wt % in Ethanol) | 0.1 |

Example 5: Preparation of Formula 5

Formula 5 was prepared by mixing together the Ingredients listed in the following table.

| Ingredients | Amount (parts by weight) |
| --- | --- |
| CITROFLEX A-4 (Acetyl Tributyl Citrate) | 45 |
| Diethyl Phthalate | 45 |
| STABAXOL 122P (Polycarbodiimide) | 10 |
| TRITON X-100 (Polyethylene Glycol Octylphenyl Ether) | 0.1 |
| Silane A171 (Vinyltrimethoxysilane) | 0.1 |
| Benzoyl Peroxide (in Diethyl Phthalate) | 0.1 |
| Silver Perchlorate (0.1 wt % in Ethanol) | 0.1 |

Example 6: Preparation of Formula 6

Formula 6 was prepared by mixing together the Ingredients listed in the following table.

| Ingredients | Amount (parts by weight) |
| --- | --- |
| CITROFLEX A-4 (Acetyl Tributyl Citrate) | 45 |
| Diethyl Phthalate | 45 |
| STABAXOL 122P (Polycarbodiimide) | 3 |
| Silane A171 (Vinyltrimethoxysilane) | 0.1 |
| TRITON X-100 (Polyethylene Glycol Octylphenyl Ether) | 0.1 |
| INDOPOL H-300 (Polybutylene Prepolymer) | 2 |
| CRODAQUAT 1207 (a cationic surfactant) | 1 |
| HERCOLYN D (Methyl Ester of Hydrogenated Rosin) | 4 |
| Methylethyl Ketone Peroxide (1 wt % in Diethyl Phthalate) | 0.1 |
| Silver Perchlorate (0.1 wt % in Ethanol) | 0.1 |

Example 7: Preparation of Formula 7

Formula 7 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 45 |
| DRAKEOL 7LT (Mineral Oil) | 7 |
| Silane A171 (Vinyltrimethoxysilane) | 0.1 |
| TRITON X-100 (Polyethylene Glycol Octylphenyl Ether) | 0.1 |
| STABAXOL 122P (Polycarbodiimide) | 3 |
| CRODAQUAT 1207 (a cationic surfactant) | 1 |
| HERCOLYN D (Methyl Ester of Hydrogenated Rosin) | 4 |
| Methylethyl Ketone Peroxide (0.1 wt % in Diethyl Phthalate) | 0.1 |
| Silver Perchlorate (0.1 wt % in Ethanol) | 0.1 |

Example 8: Preparation of Formula 8

Formula 8 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| DRAKEOL 7LT (Mineral Oil) | 7.8 |
| Silane A171 (Vinyltrimethoxysilane) | 0.1 |
| TRITON X-100 (Polyethylene Glycol Octylphenyl Ether) | 0.1 |
| CAPA 2403D (Caprolactone Polymer with 1,4-Butanediol) | 7 |
| STABAXOL 122P (Polycarbodiimide) | 3 |
| HERCOLYN D (Methyl Ester of Hydrogenated Rosin) | 5 |
| Benzoyl Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 9: Preparation of Formula 9

Formula 9 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| PLURACOL WS 2000 (Polyalkylene Glycol Derivative) | 5 |
| HERCOLYN D (Methyl Ester of Hydrogenated Rosin) | 15 |
| Silane A171 (Vinyltrimethoxysilane) | 0.1 |
| TRITON X-100 (Polyethylene Glycol Octylphenyl Ether) | 0.1 |
| Moisture Scavenger Borchi Nox M2 | 1 |
| Benzoyl Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 10: Preparation of Formula 10

Formula 10 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| TECKROS RL 5 (Rosin Esters) | 5 |
| KRASOL LBH 3000 (Hydroxy-terminated Polybutadiene) | 2 |
| IRGANOX 1010 (Pentaerythritol Tetrakis(3-(3,5-di-tert-butyl-4-hydroxyphenyl)propionate; an antioxidant) | 0.5 |
| Silane A171 (Vinyltrimethoxysilane) | 0.1 |
| CAPA 2403D (Caprolactone Polymer with 1,4-Butanediol) | 3 |
| Moisture Scavenger Borchi Nox M2 | 1 |
| Benzoyl Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 11: Preparation of Formula 11

Formula 11 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| STABAXOL 122P (Polycarbodiimide) | 5 |
| HERCOLYN D (Methyl Ester of Hydrogenated Rosin) | 5 |
| Dow Corning EL8050 (a silicone elastomer) | 3 |
| Silane A171 (Vinyltrimethoxysilane) | 0.1 |
| Benzoyl Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 12: Preparation of Formula 12

Formula 12 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| HERCOLYN D (Methyl Ester of Hydrogenated Rosin) | 10 |
| Dow Corning EL8050 (a silicone elastomer) | 2 |
| DRAKEOL 7LT (Mineral Oil) | 7 |
| COATOSIL 1770 ($\beta$-(3,4-epoxycyclohexyl ethyltriethoxysilane) | 0.1 |
| Methyl Ethyl Ketone Peroxide (0.1 wt % in Diethyl Phthalate) | 0.1 |
| Silver Perchlorate (0.1 wt % in Diethyl Phthalate) | 0.1 |

Example 13: Preparation of Formula 13

Formula 13 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| STABAXOL 122P (Polycarbodiimide) | 2 |
| HERCOLYN D (Methyl Ester of Hydrogenated Rosin) | 10 |
| Dow Corning EL8050 (a silicone elastomer) | 3 |
| DRAKEOL 7LT (Mineral Oil) | 5 |
| Silane A171 (Vinyltrimethoxysilane) | 0.1 |
| Hydrogen Peroxide (0.1 wt % in Diethyl Phthalate) | 0.1 |
| Silver Perchlorate (0.1 wt % in Diethyl Phthalate) | 0.1 |

Example 14: Preparation of Formula 14

Formula 14 was prepared by mixing together the Ingredients listed in the following table.

| Ingredients | Amount (parts by weight) |
| --- | --- |
| CITROFLEX A-4 (Acetyl Tributyl Citrate) | 39 |
| Diethyl Phthalate | 40 |
| CAPA 2403D (Caprolactone Polymer with 1,4-Butanediol) | 7 |
| DRAKEOL 7LT (Mineral Oil) | 5 |
| HERCOLYN D (Methyl Ester of Hydrogenated Rosin) | 10 |
| TRITON X-100 (Polyethylene Glycol Octylphenyl Ether) | 0.1 |
| Silane A171 (Vinyltrimethoxysilane) | 0.1 |
| Dow Corning EL8050 (a silicone elastomer) | 2 |
| Hydrogen Peroxide (0.1 wt % in Diethyl Phthalate) | 0.1 |
| Silver Perchlorate (0.1 wt % in Diethyl Phthalate) | 0.1 |

Example 15: Preparation of Formula 15

Formula 15 was prepared by mixing together the Ingredients listed in the following table.

| Ingredients | Amount (parts by weight) |
| --- | --- |
| CITROFLEX A-4 (Acetyl Tributyl Citrate) | 70 |
| Diethyl Phthalate | 12 |
| PLURONIC F127 (a PEG-PPG copolymer) | 2.5 |
| HERCOLYN D (Methyl Ester of Hydrogenated Rosin) | 15 |
| TEGO GLIDE 450 (Polyether Modified Polysiloxane) | 1 |
| Sodium Vinyl Sulfonate (a monomer) | 0.1 |
| Methyl Ethyl Ketone Peroxide (0.1 wt % in Diethyl Phthalate) | 0.1 |
| Silver Perchlorate (0.1 wt % in Diethyl Phthalate) | 0.1 |

Example 16: Preparation of Formula 16

Formula 16 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| HERCOLYN D (Methyl Ester of Hydrogenated Rosin) | 15 |
| TEGO GLIDE 450 (Polyether Modified Polysiloxane) | 2 |
| DRAKEOL 7LT (Mineral Oil) | 7 |
| STABAXOL 122P (Polycarbodiimide) | 1 |
| ARQUAD 2HT 75 (mainly Dimethyldioctadecylammonium Chloride; an anti-static agent) | 5 |
| Sodium Vinyl Sulfonate | 0.1 |
| COATOSIL 3501 (Organomodified Polydimethylsiloxane) | 0.2 |
| Methyl Ethyl Ketone Peroxide (0.1 wt % in Diethyl Phthalate) | 0.1 |
| Silver Perchlorate (0.01 wt % in Dipropylene Glycol n-Propyl Ether) | 0.1 |

Example 17: Preparation of Formula 17

Formula 17 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| STABAXOL I (containing 2,2',6,6'-Tetraisopropyldiphenyl Carbodiimide) | 3 |
| HERCOLYN D (Methyl Ester of Hydrogenated Rosin) | 10 |
| DRAKEOL 7LT (Mineral Oil) | 7 |
| MICROFLEX 1 (Alkylpyrrolidones) | 1 |
| COATOSIL 3501 (Organomodified Polydimethylsiloxane) | 0.1 |
| Methyl Ethyl Ketone Peroxide (0.1 wt % in Dipropylene Glycol n-Propyl Ether) | 0.1 |
| Silver Perchlorate (0.01 wt % in Dipropylene Glycol n-Propyl Ether) | 0.1 |

Example 18: Preparation of Formula 18

Formula 18 was prepared by mixing together the Ingredients listed in the following table.

| Ingredients | Amount (parts by weight) |
| --- | --- |
| CITROFLEX A-4 (Acetyl Tributyl Citrate) | 80 |
| PLURONIC F127 (a PEG-PPG copolymer) | 5 |
| HERCOLYN D (Methyl Ester of Hydrogenated Rosin) | 10 |
| DRAKEOL 7LT (Mineral Oil) | 5 |
| Dow Corning EL8050 (a silicone elastomer) | 6 |
| SOREZ 100 (Polyethylene Glycol Polyester) | 1 |
| COATOSIL 3501 (Organomodified Polydimethylsiloxane) | 0.2 |
| TEGO PROTECT 5000 (Hydroxy Alkyl Polydimethylsiloxane) | 1 |
| Methyl Ethyl Ketone Peroxide (0.1 wt % in Dipropylene Glycol n-Propyl Ether) | 0.1 |
| Silver Perchlorate (0.01 wt % in Dipropylene Glycol n-Propyl Ether) | 0.1 |

Example 19: Preparation of Formula 19

Formula 19 was prepared by mixing together the Ingredients listed in the following table.

| Ingredients | Amount (parts by weight) |
| --- | --- |
| CITROFLEX A-4 (Acetyl Tributyl Citrate) | 40 |
| Diethyl Phthalate | 40 |
| HERCOLYN D (Methyl Ester of Hydrogenated Rosin) | 10 |
| DRAKEOL 7LT (Mineral Oil) | 5 |
| Dow Corning EL8050 (a silicone elastomer) | 2 |
| TRITON X-100 (Polyethylene Glycol Octylphenyl Ether) | 0.1 |
| Silane A171 (Vinyltrimethoxysilane) | 0.1 |
| SURFADONE LP 300 (1-Dodecyl-2-pyrrolidone) | 2 |
| CARBOPOL 941 (Polyacrylic Acid) | 1 |
| LUPEROX DDM9 (Containing Methylethyl Ketone Peroxide) | 0.1 |
| Silver Perchlorate (0.1 wt % in Dipropylene Glycol n-Propyl Ether) | 0.1 |

Example 20: Preparation of Formula 20

Formula 20 was prepared by mixing together the Ingredients listed in the following table.

| Ingredients | Amount (parts by weight) |
|---|---|
| INDOPOL H100 (Polybutylene Prepolymer) | 100 |
| DRAKEOL 7LT (Mineral Oil) | 30 |
| Diethyl Phthalate | 30 |
| CITROFLEX A-4 (Acetyl Tributyl Citrate) | 20 |
| ECOSURF SA-7 | 2 |
| PLURONIC F-64 (a PEG-PPG copolymer) | 1.5 |
| TEGO GLIDE 450 (Polyether Modified Polysiloxane) | 0.5 |
| Silane A171 (vinyltrimethoxysilane) | 0.1 |
| Urea Peroxide (0.01 wt % in Dipropylene Glycol n-Propyl Ether) | 0.1 |
| Silver Perchlorate (0.1 wt % in Dipropylene Glycol n-Propyl Ether) | 0.1 |

Example 21: Preparation of Formula 21

Formula 21 was prepared by mixing together the Ingredients listed in the following table.

| Ingredients | Amount (parts by weight) |
|---|---|
| CITROFLEX A-4 (Acetyl Tributyl Citrate) | 42 |
| Diethyl Phthalate | 82 |
| HERCOLYN D (Methyl Ester of Hydrogenated Rosin) | 3.5 |
| PLURONIC F-64 (a PEG-PPG copolymer) | 0.5 |
| TEGO GLIDE 450 (Polyether Modified Polysiloxane) | 0.5 |
| Ferrous Ammonium Sulfate (0.1 wt % in Dipropylene Glycol n-Propyl Ether) | 0.1 |
| Urea Peroxide (0.1 wt % in Dipropylene Glycol n-Propyl Ether) | 0.1 |

Example 22: Preparation of Formula 22

Formula 22 was prepared by mixing together the Ingredients listed in the following table.

| Ingredients | Amount (parts by weight) |
|---|---|
| DRAKEOL 7LT (Mineral Oil) | 60 |
| Diethyl Phthalate | 10 |
| INDOPOL H100 (Polybutylene Prepolymer) | 6 |
| IGEPAL CO-630 (Polyoxyethylene nonylphenylether) | 1 |
| PLURONIC F-64 (a PEG-PPG copolymer) | 1 |
| COATOSIL 3501 (Organomodified Polydimethylsiloxane) | 0.1 |
| DOWANOL PnP (Dipropylene Glycol n-Propyl Ether) | 21 |
| Silane A171 (vinyltrimethoxysilane) | 0.1 |
| Urea Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 23: Preparation of Formula 23

Formula 23 was prepared by mixing together the Ingredients listed in the following table.

| Ingredients | Amount (parts by weight) |
|---|---|
| DOWANOL PnP (Dipropylene Glycol n-Propyl Ether) | 15 |
| INDOPOL H100 (Polybutylene Prepolymer) | 4 |
| Diethyl Phthalate | 80 |
| CITROFLEX A-4 (Acetyl Tributyl Citrate) | 22 |
| PLURONIC F-64 (a PEG-PPG copolymer) | 3 |
| HERCOLYN D (Methyl Ester of Hydrogenated Rosin) | 22.5 |
| DRAKEOL 7LT (Mineral Oil) | 10 |
| ECOSURF SA-7 | 0.5 |
| IGEPAL CO-630 (Polyoxyethylene nonylphenylether) | 0.5 |
| Urea Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 24: Preparation of Formula 24

Formula 24 was prepared by mixing together the Ingredients listed in the following table.

| Ingredients | Amount (parts by weight) |
|---|---|
| INDOPOL H100 (Polybutylene Prepolymer) | 6 |
| DRAKEOL 7LT (Mineral Oil) | 71 |
| HERCOLYN D (Methyl Ester of Hydrogenated Rosin) | 20 |
| PLURONIC F-127 (a PEG-PPG copolymer) | 1 |
| ECOSURF SA-7 | 2 |
| COATOSIL 1770 (β-(3,4-epoxycyclohexyl ethyltriethoxysilane) | 0.1 |
| COATOSIL 3501 (Organomodified Polydimethylsiloxane) | 0.1 |
| Urea Peroxide (0.01 wt % in Dipropylene Glycol n-Propyl Ether) | 0.1 |
| Silver Perchlorate (0.1 wt % in Dipropylene Glycol n-Propyl Ether) | 0.1 |

Example 25: Preparation of Formula 25

Formula 25 was prepared by mixing together the Ingredients listed in the following table.

| Ingredients | Amount (parts by weight) |
|---|---|
| INDOPOL H100 (Polybutylene Prepolymer) | 8 |
| Diethyl Phthalate | 160 |
| PLURONIC F-127 (a PEG-PPG copolymer) | 6 |
| HERCOLYN D (Methyl Ester of Hydrogenated Rosin) | 67 |
| DRAKEOL 7LT (Mineral Oil) | 60 |
| ECOSURF SA-7 | 0.5 |
| FLUOROSURFACTANT FC 4432 (a non-ionic fluoropolymer surfactant) | 0.25 |
| SURFADONE LP 100 (Caprylyl Pyrrolidone) | 0.5 |
| COATOSIL 3501 (Organomodified Polydimethylsiloxane) | 0.25 |
| COATOSIL 1770 (β-(3,4-epoxycyclohexyl ethyltriethoxysilane) | 0.1 |
| Urea Peroxide (0.1 wt % in Dipropylene Glycol n-Propyl Ether) | 0.1 |
| Silver Perchlorate (0.1 wt % in Dipropylene Glycol n-Propyl Ether) | 0.1 |

Example 26: Preparation of Formula 26

Formula 26 was prepared by mixing together the Ingredients listed in the following table.

| Ingredients | Amount (parts by weight) |
|---|---|
| INDOPOL H100 (Polybutylene Prepolymer) | 35 |
| Diethyl Phthalate | 160 |
| PLURONIC F-127 (a PEG-PPG copolymer) | 6 |
| HERCOLYN D (Methyl Ester of Hydrogenated Rosin) | 105 |
| DRAKEOL 7LT (Mineral Oil) | 60 |
| DOWANOL PnP (Dipropylene Glycol n-Propyl Ether) | 70 |
| ECOSURF SA-7 | 4 |
| Silane A171 (vinyltrimethoxysilane) | 1.5 |
| COATOSIL 1770 (β-(3,4-epoxycyclohexyl ethyltriethoxysilane) | 0.25 |
| Dow Corning EL8050 (a silicone elastomer) | 6 |
| Silver Perchlorate (0.1 wt % in Dipropylene Glycol n-Propyl Ether) | 4 |
| Benzoyl Peroxide (0.1 wt % in Dipropylene Glycol n-Propyl Ether) | 1 |

Example 27: Preparation of Formula 27

Formula 27 was prepared by mixing together the Ingredients listed in the following table.

| Ingredients | Amount (parts by weight) |
|---|---|
| INDOPOL H100 (Polybutylene Prepolymer) | 2 |
| CITROFLEX A-4 (Acetyl Tributyl Citrate) | 40 |
| PLURONIC F-127 (a PEG-PPG copolymer) | 1.5 |
| HERCOLYN D (Methyl Ester of Hydrogenated Rosin) | 20.5 |
| DRAKEOL 7LT (Mineral Oil) | 15 |
| DOWANOL PnP (Dipropylene Glycol n-Propyl Ether) | 12.5 |
| ECOSURF SA-7 | 0.12 |
| Silane A171 (vinyltrimethoxysilane) | 0.1 |
| COATOSIL 1770 (β-(3,4-epoxycyclohexyl ethyltriethoxysilane) | 0.05 |
| Silver Perchlorate (0.1 wt % in Dipropylene Glycol n-Propyl Ether) | 0.05 |
| Urea Peroxide (0.1 wt % in Dipropylene Glycol n-Propyl Ether) | 0.05 |
| PLURACOL WS 2000 (Polyalkylene Glycol Derivative) | 1 |

Example 28: Preparation of Formula 28

Formula 28 was prepared by mixing together the Ingredients listed in the following table.

| Ingredients | Amount (parts by weight) |
|---|---|
| INDOPOL H100 (Polybutylene Prepolymer) | 4 |
| HERCOLYN D (Methyl Ester of Hydrogenated Rosin) | 41 |
| Benzyl Benzoate | 40 |
| Terpene | 70 |
| DRAKEOL 7LT (Mineral Oil) | 25 |
| ECOSURF SA-7 | 0.5 |
| Silane A171 (Vinyltrimethoxysilane) | 0.1 |
| COATOSIL 3501 (Organomodified Polydimethylsiloxane) | 0.05 |
| PLURACOL WS 2000 (Polyalkylene Glycol Derivative) | 1 |
| Urea Peroxide (0.1 wt % in Benzoate) | 0.05 |
| Silver Perchlorate (0.1 wt % in Benzoate) | 0.05 |

Example 29: Evaluation of Formula 28 in a Liquid Laundry Detergent (LLD)

Sample Preparation

Formula 28 (10 g; 25 wt %) and a fragrance (or a fragrance mixture) (30 g; 75 wt %) was mixed and stirred until homogenous to form an intermediate mixture (40 g), which is referred to as "a bullet" hereinafter. When a fragrance mixture containing an aldehyde and an amine was used, the aldehyde and amine were mixed and permitted to stand for 24 hours at room temperature to allow formation of a Schiff base prior to the addition of formula 28. The bullet thus formed (40 g; 62.5 wt %) was then mixed with an accompanying fragrance mixture "Floral Bouquet" (24 g; 37.5 wt %) (Robertet Inc., Oakland, N.J.) to form a blend (64 g). The blend thus formed was stirred until homogenous and allowed to stand for 24 hours at room temperature. The blend was then added to a 2× concentrated LLD base at a percentage of 0.8 wt % to form a LLD test sample, which was allowed to stand for 24 hours at room temperature before use.

Washing and Drying Procedures

A heavy duty super capacity top load washing machine (model #GTUP270GM0WW; GE Appliances, Louisville Ky.) was set at the "Warm/Cold," "Large Load," and "Agitate on Cottons Regular/Fast-Medium" settings. After the washing machine was filled with water to about ⅓ of its volume, a detergent containing the LLD test sample described in the preceding paragraph and 22 100% cotton white wash cloths were sequentially added into the washing machine. After the lid was closed, the washing machine was allowed to run a complete washing cycle. A commercially available detergent, Tide® Liquid Detergent 2× Concentrated with Febreze Spring & Renewal® (Procter and Gamble, Cincinnati, Ohio), was used a LLD control sample.

After washing was completed, the cloths were dried. A heavy duty super capacity dryer (model # GTUP270GM0WW; GE Appliances, Louisville Ky.) was set at the "Low Heat Whites" and "60 Minutes Timed Dry" settings. The damp wash cloths were transferred from the washing machine to the dryer, which was allowed to run a complete cycle.

Evaluation Method 20 consumers were enlisted to evaluate the strength and duration of the fragrance on the washed and dried cloths. The consumers had the following characteristics: (1) heads of household, (2) who prefer fragranced detergent, (3) non-smokers, (4) not pregnant, and (5) responsible for purchasing laundry detergent. During the evaluation process, each consumer smelled a wash cloth washed by a test sample detergent and a wash cloth washed by a control detergent. Specifically, each consumer picked up one wash cloth with tongs to smell it, scored it on a scale of 1-7 (1 being the lowest fragrance strength and 7 being the highest fragrance strength), and then discarded it in a separate bin. The wash cloths were then saved and smelled again in the next day by the same group of consumers. When the test sample detergents and control detergent were evaluated by the same group of consumers, the sequence of the wash clothes washed by these detergents to be smelled by each consumer was rotated to eliminate first sniff bias. The evaluation process was continued for a two-week period.

Results 23 fragrances were used in the above test to evaluate their fragrance strength and duration after washing and drying. The results are summarized in Table 1 below.

TABLE 1

|    | INCI Name | CAS Number | Olfactory Description | Lowest Strength | Highest Strength | Day Strength was Lowest | Day Strength Peaked |
|----|-----------|------------|----------------------|-----------------|------------------|-------------------------|---------------------|
| 1  | 2,4-dimethyl-4,4a,5,9b-tetrahydroindeno[1,2-d][1,3]dioxine | 27606-09-3 | Floral, green, magnolia, peony, geranium lily of valley note | 2.5 | 2.8 | 0 | 6 |
| 2  | 4-(4-Hydroxy-4-methylpentyl)-3-cyclohexene-1-carboxaldehyde | 31906-04-4 | Soft, delicate, floral, lily, cyclamen, lilac note | 1.8 | 2.8 | 0 | 2 |
| 3  | 3,7-dimethylocta-1,6-dien-3-ol | 78-70-6 | Floral w/citrus and woody notes. Used for lavender notes and bergamot | 2.6 | 3.0 | 1 | 3 |
| 4  | 3,7-dimethyl-1,7-octane diol | 107-74-4 | Muguet, floral, sweet, green, fruity melon notes | 1.9 | 3.2 | 1 | 4 |
| 5  | 2-(phenylmethylidene)octanal | 101-86-0 | Floral, jasmin, waxy, aromatic, sweet, fruity | 2.9 | 3.8 | 7 | 14 |
| 6  | methyl 2-aminobenzoate | 134-20-3 | Fruity, floral, orange blossom, grape | 2.1 | 3.9 | 4 | 2 |
| 7  | guaiol acetate | 61789-17-1 | Sweet woody | 2.6 | 4.0 | 0 | 9, 12 |
| 8  | 2-benzylideneheptanal | 122-40-7 | Floral, jasmine, waxy | 2.8 | 4.1 | 2, 7, 8 | 14 |
| 9  | 3-(4-tert-butylphenyl)butanal | 80-54-6 | Floral muguet watery green powdery cumin | 2.3 | 4.3 | 0 | 4 |
| 10 | 3,7-dimethyloct-6-enenitrile | 51566-62-2 | Fresh, lemon, metallic citrus, waxy, floral | 3.3 | 4.3 | 1 | 4, 12 |
| 11 | 4-methoxy benzaldehyde | 123-11-5 | Anisic | 3.6 | 4.4 | 1 | 6 |
| 12 | 2-(4-methylcyclohexyl)propan-2-yl acetate | 58985-18-5 | Pine, citrus, woody, lime cologne | 3.7 | 4.4 | 1, 14 | 6 |
| 13 | dodecanal | 112-54-9 | Fatty, woody, herbaceous, floral, citrus | 2.6 | 4.5 | 0 | 14 |
| 14 | (E)-4-(2,6,6-trimethyl-1-cyclohex-2-enyl)but-3-en-2-one | 127-41-3 | Sweet, woody, floral violet, orris, tropical fruity | 3.8 | 4.7 | 5 | 7 |
| 15 | methyl cedryl ketone | 32388-55-9 | Woody, vetiver amber, leather, musk, cedar | 4.3 | 5.1 | 1 | 12 |
| 16 | 2,6-dimethylhept-5-enal | 106-72-9 | Fresh ozone, melon, fresh air sweet clean green | 4.1 | 5.2 | 1 | 3 |
| 17 | (E)-4-(2,6,6-trimethyl-1-cyclohexenyl)but-3-en-2-one | 14901-07-6 | Violet, orris sweet, floral, woody | 3.9 | 5.6 | 6 | 3 |
| 18 | (Z)-3-methyl-5-(2,2,3-trimethyl-1-cyclopent-3-enyl)pent-4-en-2-ol | 67801-20-1 | Sandalwood, musk | 4.4 | 5.9 | 6 | 1 |
| 19 | benzaldehyde | 100-52-7 | Strong, sharp, sweet, bitter almond cherry | 3.6 | 4.4 | 5 | 3 |
| 20 | ethyl 2-methylbutanoate | 7452-79-1 | Fruity, estry & berry w/fresh tropical nuances | 3.7 | 4.6 | 5 | 12 |
| 21 | exan-1-ol | 111-27-3 | Ethereal fusel oil, fruity alcoholic sweet green | 3.4 | 4.4 | 5 | 12 |
| 22 | 2-(4-methyl-1-cyclohex-3-enyl)propan-2-ol | 98-55-5 | Pine terpene, lilac, citrus, woody, floral | 3.6 | 4.3 | 5 | 12 |
| 23 | methyl 2-aminobenzoate | 134-20-3 | Fruity, floral, orange blossom, grape | 2.1 | 3.9 | 4 | 2 |

In addition, 17 fragrance mixtures (each containing a fragrance listed in Table 2 below and methyl 2-aminobenzoate) used in the above test to evaluate their fragrance strength duration after washing and drying. The results are summarized in Table 2 below.

TABLE 2

|  | INCI Name | CAS # | Odor | Lowest Strength Average | Highest Strength Average | Day Strength was Lowest | Day Strength Peaked |
|---|---|---|---|---|---|---|---|
| 24 | benzaldehyde | 100-52-7 | Almond, cherry, sweet | 3.2 | 3.8 | 1, 8 | 6 |
| 25 | 1-methyl-4-(4-methylpentyl)cyclohex-3-ene-1-carbaldehyde | 66327-54-6 | Natural, green, agrestic, fresh, aldehydic | 3.3 | 3.8 | 3, 6 | 0 |
| 26 | 4-propan-2-ylbenzaldehyde | 122-03-2 | Spicy, green, cumin-like, herbal | 3.0 | 3.9 | 0 | 10 |
| 27 | 3-(4-propan-2-ylphenyl)butanal | 103-95-7 | Floral, cyclamen, fresh rhubarb musty green | 3.8 | 4.1 | 6 | 1 |
| 28 | 1,3-benzodioxole-5-carbaldehyde | 120-57-0 | Very sweet floral, warm slightly spicy, cherry-like | 3.0 | 4.1 | 6 | 7 |
| 29 | 3-(4-tert-butylphenyl)butanal | 80-54-6 | Floral, muguet, watery, green, powerful, cumin | 3.4 | 4.1 | 7 | 6 |
| 30 | 2,4-dimethyl cyclohex-3-ene-1-carbaldehyde | 68039-49-6 | Green, leafy, floral, powerful | 3.0 | 4.1 | 0 | 3, 6 |
| 31 | 1,1-dimethoxy propan-2-ylbenzene | 90-87-9 | Green with rose leaf odor and mushroom note | 3.3 | 4.4 | 6 | 11 |
| 32 | dodec-3-enal | 68083-57-8 | Bitter, orange, mandarin, coriander | 4.0 | 4.5 | 1 | 0 |
| 33 | dodecanal | 112-54-9 | Fresh, citrus, 'natural' fattiness | 3.7 | 4.8 | 2 | 10 |
| 34 | 3-(3-propan-2-ylphenyl)butanal | 125109-85-5 | Floral, green, muguet, fresh, powerful | 3.0 | 4.8 | 0 | 7 |
| 35 | 2-benzylidene heptanal | 122-40-7 | Floral, jasmine, waxy | 3.8 | 4.9 | 0 | 10 |
| 36 | 3-phenylprop-2-enal | 104-55-2 | Sweet, balsamic, cinnamon, faint almond | 3.3 | 5.0 | 14 | 4 |
| 37 | 3-(1,3-benzodioxol-5-yl)-2-methylpropanal | 1205-17-0 | Watery, floral, fresh, green ozone cyclamen hay | 3.8 | 5.1 | 6 | 14 |
| 38 | 3-(4-methoxy phenyl)-2-methylpropanal | 005462-06-6 | Licorice, basil, fennel, anise notes w/slight fruity, watery modification | 4.3 | 5.2 | 6 | 13 |
| 39 | 2-phenylpropanal | 93-53-8 | Fresh, green, leafy-floral, tart, hyacinth | 3.5 | 5.5 | 1 | 0 |
| 40 | 2-phenyl acetaldehyde | 122-78-1 | Very strong, green hyacinth, floral | 5.1 | 6.3 | 0 | 7, 8 |

Figure 2:
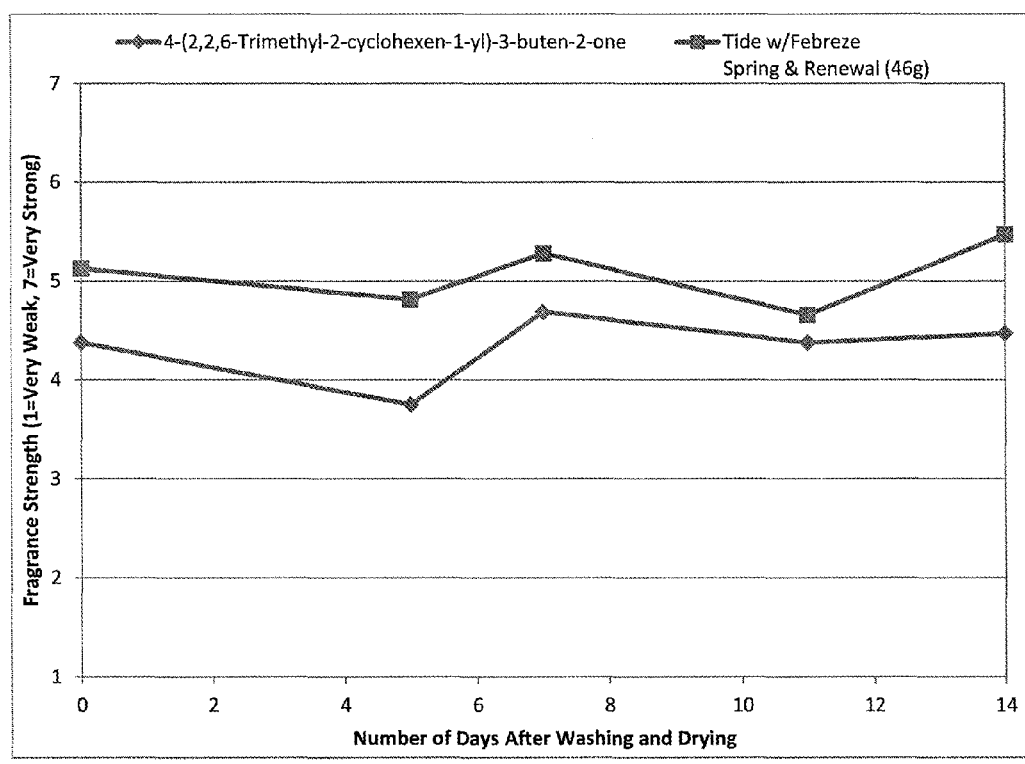
FIG. 2 is a graph comparing the fragrance strength and duration between a LLD control sample and a LLD test sample containing Formula 28 and (E)-4-(2,6,6-trimethyl-1-cyclohexenyl)but-3-en-2-one.
Figure 3:
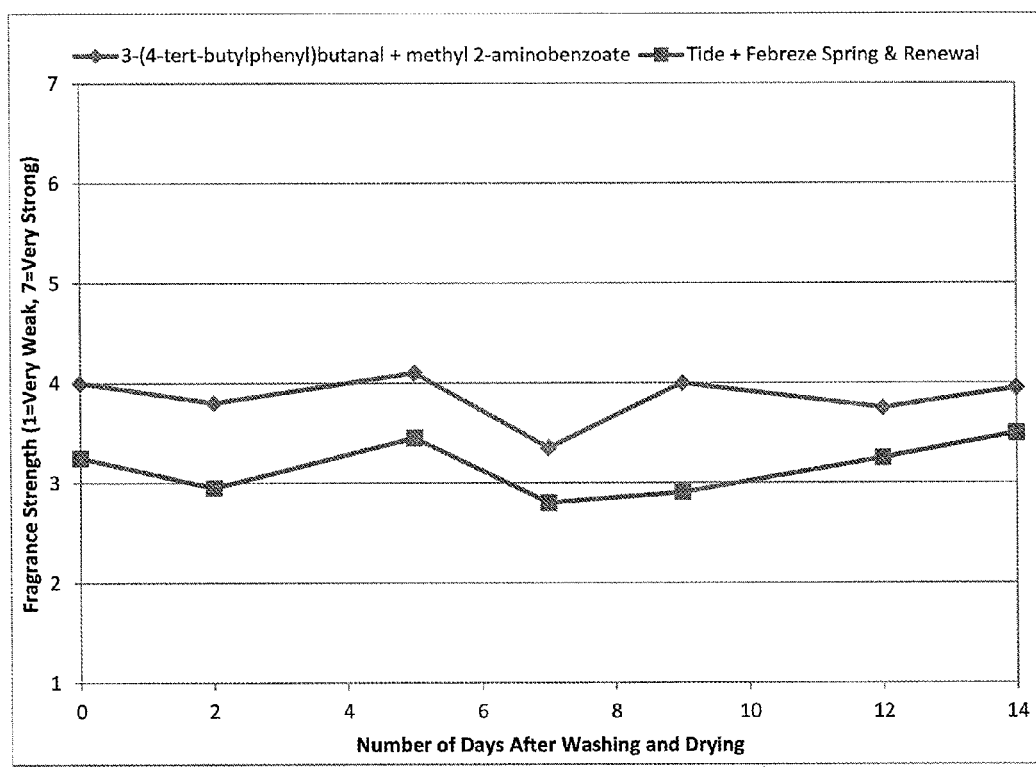
FIG. 3 is a graph comparing the fragrance strength and duration between a LLD control sample and a LLD test sample containing Formula 28, 3-(4-tert-butylphenyl)butanal, and methyl 2-aminobenzoate.

FIGS. 1-3 show more detailed results obtained from fragrance Nos. 7, 17, and 29, respectively. Each data point in these figures is an average value of the scores obtained from 20 consumers.

The results demonstrated that LLD test samples (i.e., containing Formula 28 and a single fragrance compound or a fragrance mixture) exhibited similar or superior fragrance strength and duration compared to the LLD control sample.

Example 30: Evaluation of Formula 28 in a Liquid Fabric Softener

Formula 28 was evaluated for its efficacy in keeping a washed/dried cloth fragranced when used in combination with a liquid fabric softener as follows:
Sample Preparation Formula 28 was used to form a liquid fabric softener sample in the same manner as that described in Example 29 except that the 2× concentrated LLD base in the LLD test sample was replaced with a 3× concentrated liquid fabric softener base and that the bullet/fragrance blend was added to the liquid fabric softener base at a percentage of 1.2 wt % instead of 0.8 wt %.
Washing and Drying Procedures A heavy duty super capacity top load washing machine (model # GTUP270GM0WW; GE Appliances, Louisville Ky.) was set at the "Warm/Cold," "Large Load," and "Agitate on Cottons Regular/Fast-Medium" settings. After the washing machine was filled with water to about ⅓ of its volume, 50 g of a Free & Clear® LLD (Henkel Company, Scottsdale, Ariz.) and 22 100% cotton white wash cloths were sequentially added into the washing machine. After the lid was closed, the washing machine was allowed to run to the rinse cycle. The washing machine was again filled with water to about ⅓ of its volume. A liquid fabric softener test sample was then added into the washing machine. The washing machine was then allowed to run until a full washing cycle was completed.

After washing was completed, the cloths were dried. A heavy duty super capacity dryer (model # GTUP270GM0WW; GE Appliances, Louisville Ky.) was set at the "Low Heat Whites" and "60 Minutes Timed Dry" settings. The damp wash cloths were transferred from the washing machine to the dryer, which was allowed to run a complete cycle.
Evaluation Method The washed and dried cloths were evaluated for their fragrance strength and duration in the same manner as described in Example 29 except that a panel of 20 experts (instead of consumers) were used to conduct the evaluation.
Results Three liquid fabric softener test samples were prepared using Formula 28 and a fragrance mixture following the procedures described above: (1) sample 1 contained a fragrance mixture of 3-(4-methoxyphenyl)-2-methyl propanal and methyl 2-aminobenzoate; sample 2 contained a fragrance mixture of 2,4-dimethylcyclohex-3-ene-1-carbaldehyde and methyl 2-aminobenzoate; and sample 3 contained a fragrance mixture of 2-phenylacetaldehyde and methyl 2-aminobenzoate. Downy Ultra April Fresh (Procter & Gamble, Cincinnati, Ohio) was used as a liquid fabric softener control sample.

Figure 4:
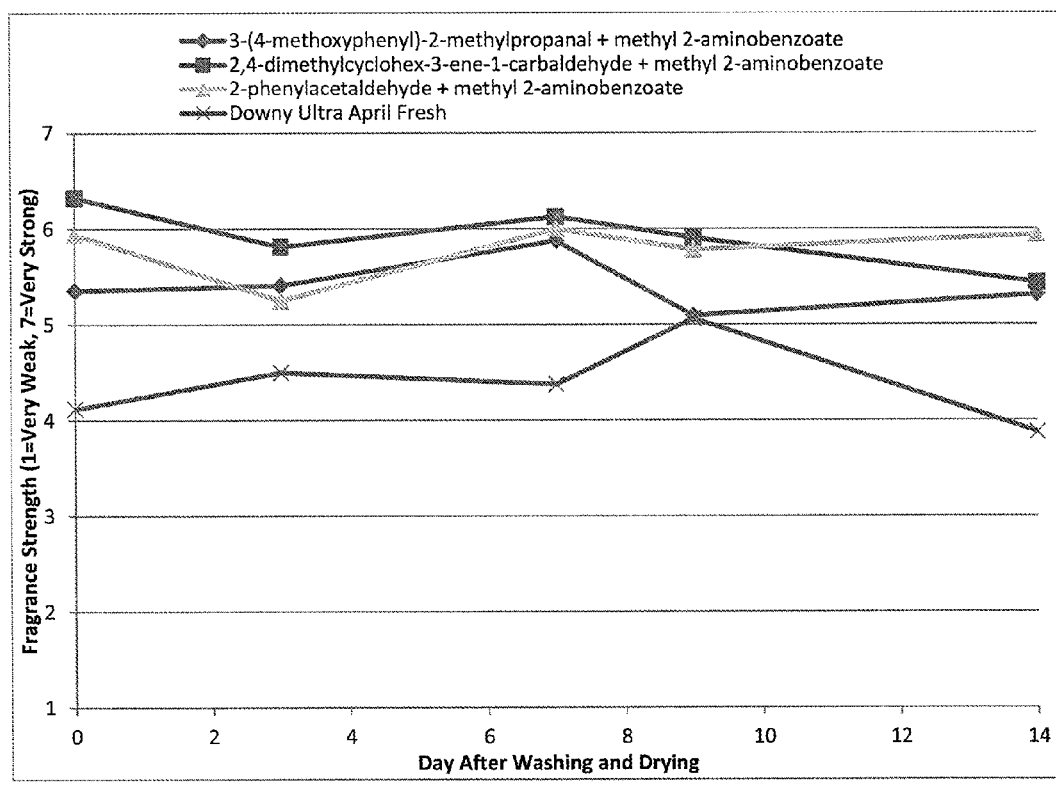
FIG. 4(A) is a graph comparing the fragrance strength and duration between a liquid fabric softener control sample and a liquid fabric softener test sample containing Formula 28 and different fragrances.
FIG. 4(B) is a graph comparing the fragrance strength and duration between a liquid fabric softener control sample and a liquid fabric softener test sample containing different amounts of Formula 28 and White Pearl.

FIG. 4A shows the results obtained from the above three liquid fabric softener test samples. The results demonstrated that the liquid fabric softener test samples exhibited similar or superior fragrance strength and duration compared to the liquid fabric softener control sample.

In addition, four liquid fabric softener test samples were prepared using different amounts of a White Pearl fragrance mixture ("White Pearl") (Robertet Inc., Oakland, N.J.) and Formula 28 following the procedures described above: (1) sample 1 contained only White Pearl with no Formula 28; (2) sample 2 contained 85 wt % White Pearl and 15 wt % Formula 28; (3) sample 3 contained 75 wt % White Pearl and 25 wt % Formula 28; and (4) sample 4 contained 65 wt % White Pearl and 35 wt % Formula 28. Flor Frescor Azul® (Reckitt Benckiser, Granollers, Spain) was used as a control liquid fabric softener sample.

Figure 4B:
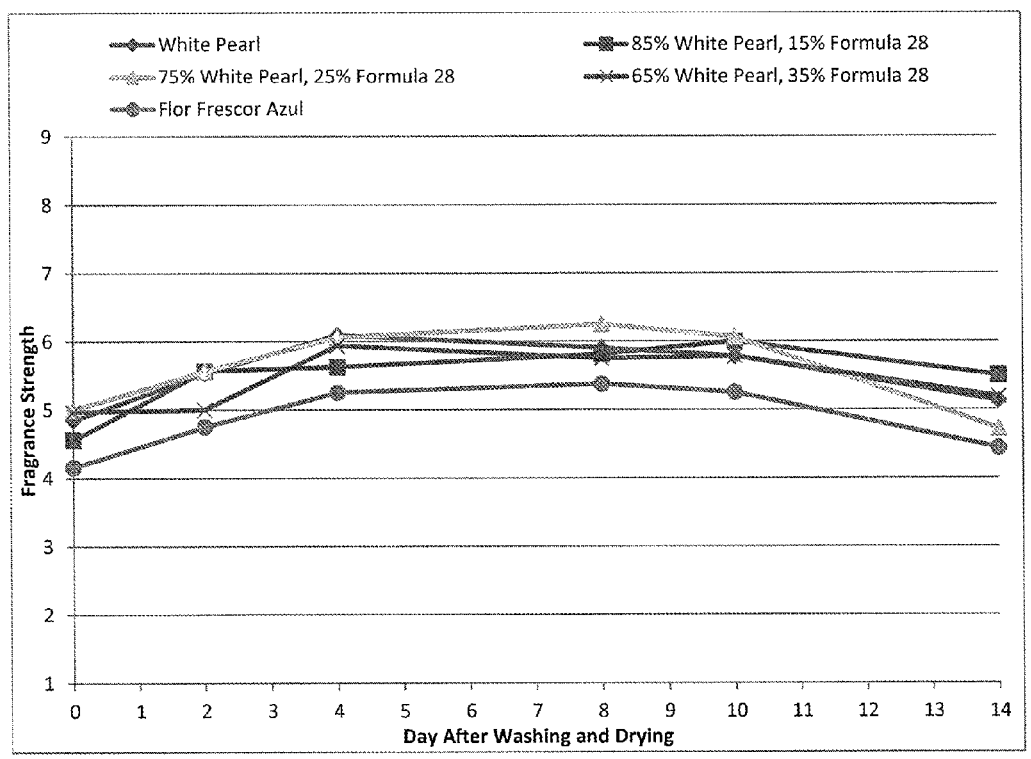

FIG. 4B shows the results obtained from the above four liquid fabric softener test samples. The results demonstrated that these liquid fabric softener test samples exhibited superior fragrance strength and duration compared to the liquid fabric softener control sample. In addition, samples 2-4 exhibited similar fragrance strength and duration compared to sample 1 even though they included smaller amounts of fragrance than sample 1.

Example 31: Evaluation of Formula 28 in a Dryer Sheet

Sample Preparation

A fragranced dryer sheet sample was prepared as follows: A 15×14 inch non-stick cookie sheet was first placed on a Thermolyne® Nuova™ heating plate. The cookie sheet was kept at 115° C. on the heating plate during the entire procedure. A quaternary ammonium salt (which can impart softness to the dryer sheet) was heated to 50° C. in an 85° C. hot water bath. On a balance, 0.18 g of a composition containing a fragrance (with or without formula 28) was combined with 3.82 g of the quaternary ammonium salt. The fragranced quaternary ammonium salt was then heated to 50° C. again in an 85° C. hot water bath. A 9×5.5 inch dryer sheet was placed on top of an 11×7.5 inch Reynolds Genuine Parchment Paper. The parchment paper and dryer sheet were then placed on a balance. After the fragranced quaternary ammonium salt was removed from the hot water bath, 0.89 g of the fragranced quaternary ammonium salt was transferred onto the dryer sheet. The parchment paper, dryer sheet and fragranced quaternary ammonium salt were then transferred onto the cookie sheet. The sample thus formed was allowed to completely melt into dryer sheet. Simultaneously, a second piece of 11×7.5 inch Reynolds Genuine Parchment Paper was placed on a different portion of the non-stick cookie sheet mentioned above and warmed to 110° C. Once warmed to 110° C., the parchment paper was placed on top of the dryer sheet. The sample remained on the heating plate while the fragranced quaternary ammonium salt was uniformly spread over the dryer sheet on both sides by using a rolling pin (starting from the middle and working toward all the edges). The sample was then allowed to cool down to room temperature. A dryer sheet sample containing a fragrance was formed after removing the parchment papers. An un-fragranced dryer sheet was prepared using the same procedure described above except that no fragrance was added.
Washing and Drying Procedures A heavy duty super capacity top load washing machine (model # GTUP270GM0WW; GE Appliances, Louisville Ky.) was set at the "Warm/Cold," "Large Load," and "Agitate on Cottons Regular/Fast-Medium" settings. After the washing machine was filled with water to about ⅓ of its volume, 50 g of a Free & Clear® LLD (Henkel Company, Scottsdale, Ariz.) and 22 100% cotton white wash cloths were sequentially added into the washing machine. After the lid was closed, the washing machine was allowed to run a complete washing cycle.

After washing was completed, the cloths were dried. A dryer sheet was added into a heavy duty super capacity dryer (model # GTUP270GM0WW; GE Appliances, Louisville Ky.), which was then set at the "Low Heat Whites" and "60 Minutes Timed Dry" settings. The damp wash cloths were transferred from the washing machine to the dryer. The dryer was allowed to run a complete cycle.

Evaluation Method

The washed and dried cloths were evaluated for their fragrance strength and duration in the same manner as described in Example 30.

Results

Three dryer sheet samples were prepared using different amounts of a Floral Bouquet fragrance ("Floral Bouquet") and Formula 28 following the procedures described above: (1) sample 1 contained only Floral Bouquet with no Formula 28; (2) sample 2 contained 89.82 wt % Floral Bouquet and 10.18 wt % Formula 28; and (3) sample 3 contained 75 wt % Floral Bouquet and 25 wt % Formula 28. A un-fragranced dryer sheet was used as a control sample.

Figure 5:
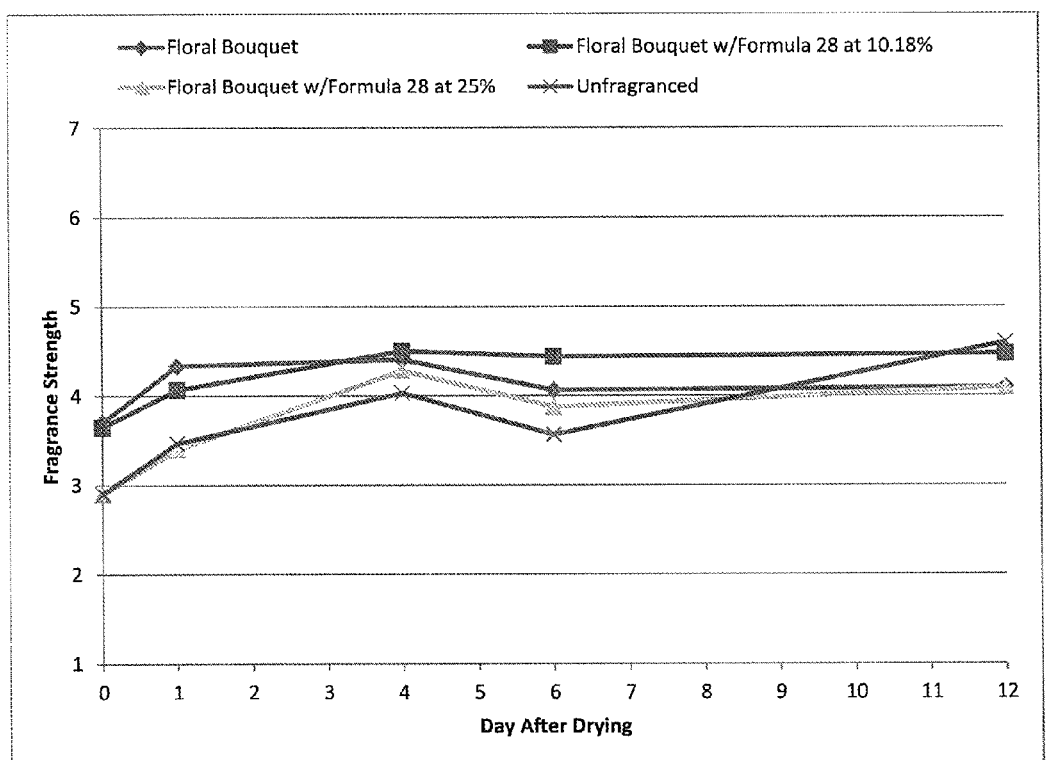
FIG. 5 is a graph comparing the fragrance strength and duration between a dryer sheet control sample and a dryer sheet test sample containing different amounts of Formula 28 and Floral Bouquet.
Figure 6A:
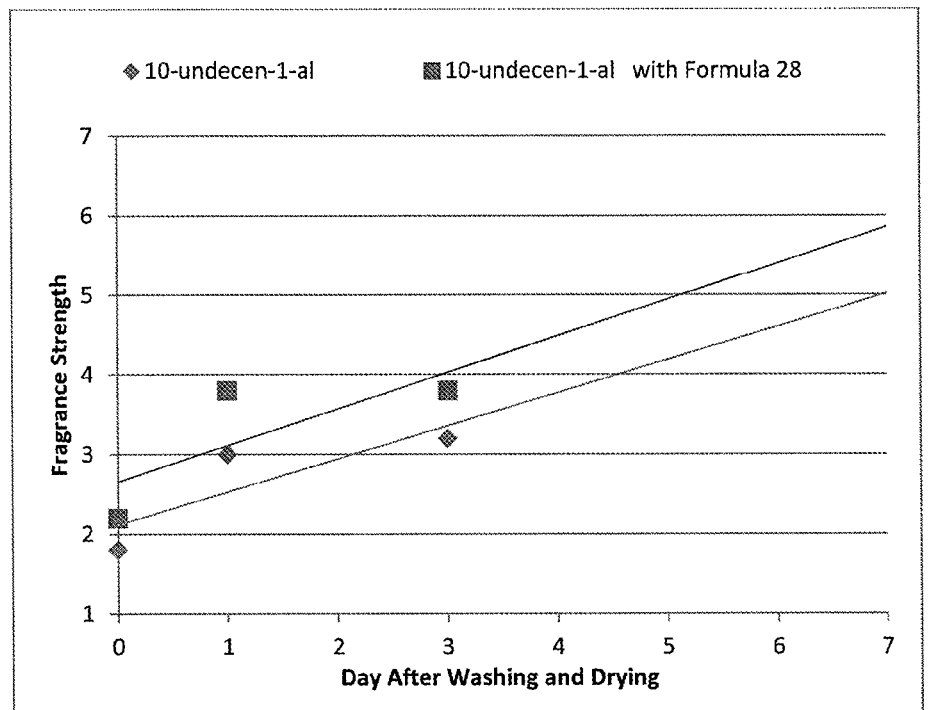
FIG. 6(A) is a graph comparing the fragrance strength and duration between a LLD test sample containing 10-undecen-1-al without Formula 28 and a LLD test sample containing 10-undecen-1-al and Formula 28.
Figure 6B:
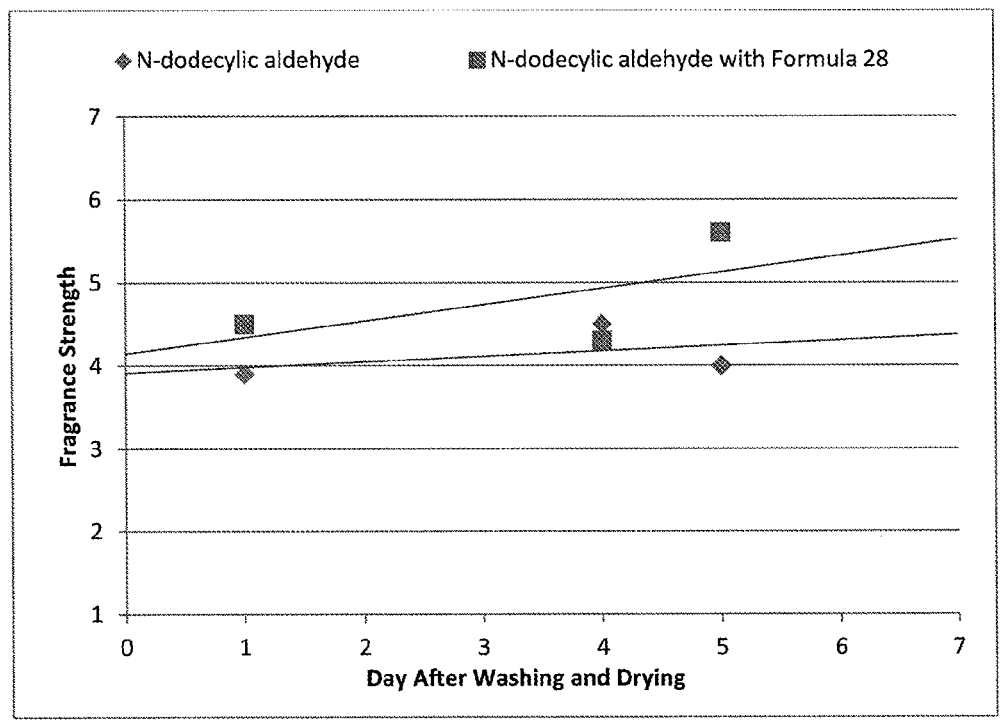
FIG. 6(B) is a graph comparing the fragrance strength and duration between a LLD test sample containing n-dodecanal without Formula 28 and a LLD test sample containing n-dodecanal and Formula 28.
Figure 6C:
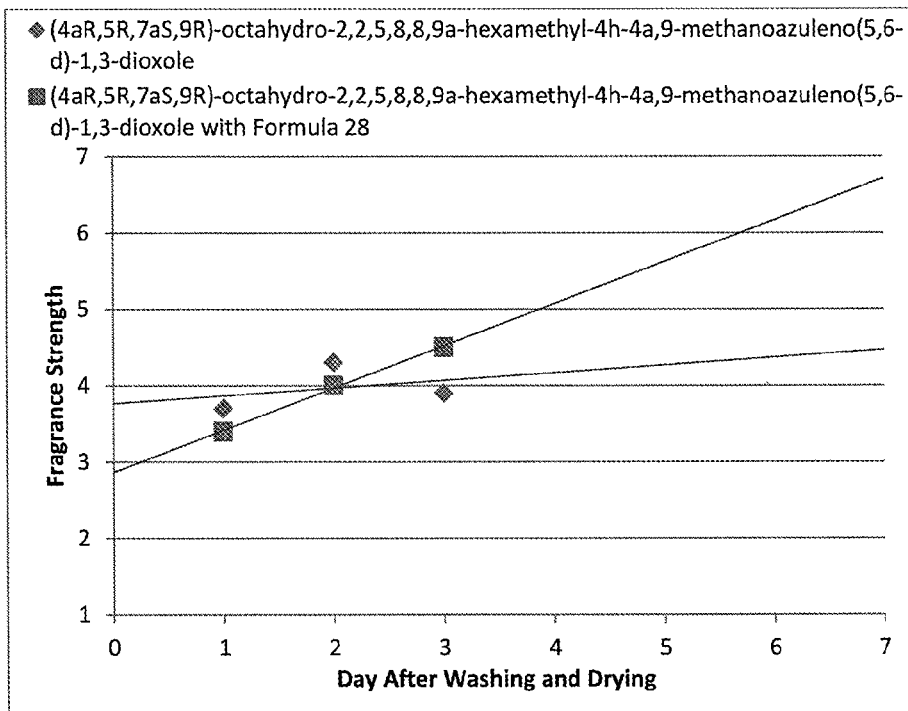
FIG. 6(C) is a graph comparing the fragrance strength and duration between a LLD test sample containing (4aR,5R,7aS,9R)-octahydro-2,2,5,8,8,9a-hexamethyl-4H-4-a,9-methanozuleno[5,6-d]-1,3-dioxole without Formula 28 and a LLD test sample containing (4aR,5R,7aS,9R)-octahydro-2,2,5,8,8,9a-hexamethyl-4H-4-a,9-methanozuleno[5,6-d]-1,3-dioxole and Formula 28.
Figure 6D:
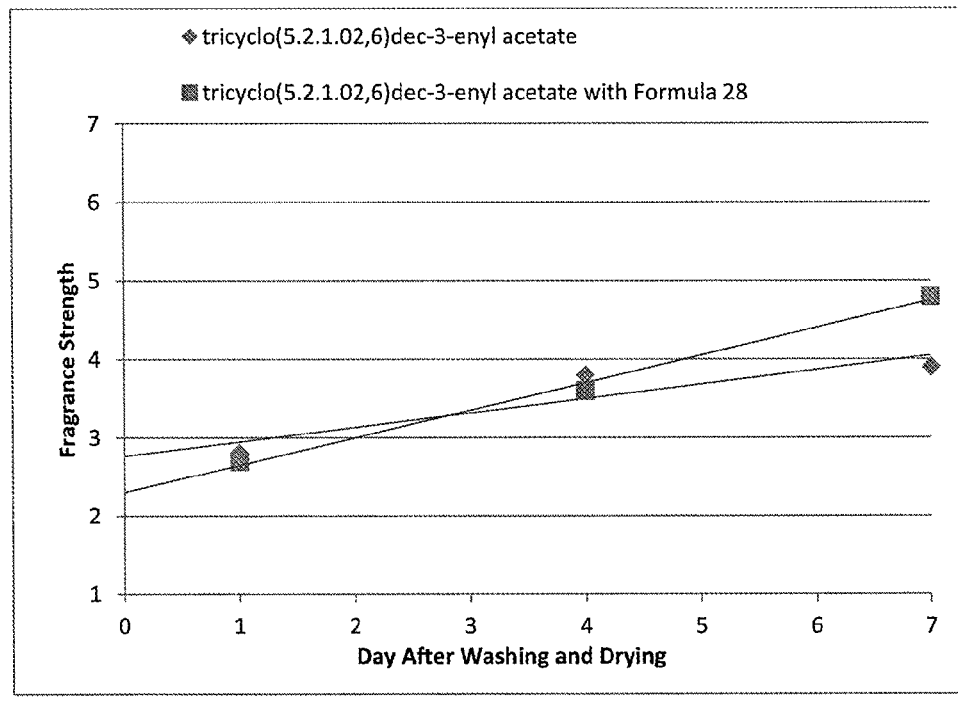
FIG. 6(D) is a graph comparing the fragrance strength and duration between a LLD test sample containing tricyclo(5.2.1.02,6)dec-3-enyl acetate without Formula 28 and a LLD test sample containing tricyclo(5.2.1.02,6)dec-3-enyl acetate and Formula 28.

FIG. 5 shows the results obtained from the above test. The results demonstrated that the control sample (i.e., the un-fragranced dryer sheet) developed a strong unpleasant odor during the test (possibly due to oxidation of the quaternary ammonium salt). By contrast, the fragranced dryer sheet samples inhibited the unpleasant odor and exhibited superior fragrance strength and duration. In addition, samples 2 and 3 exhibited similar or better fragrance strength and duration compared to sample 1 even though they included smaller amounts of fragrance than sample 1.

Example 32: Comparison of LLD Samples Containing Various Fragrances with and without Formula 28

LLD samples containing a fragrance with and without Formula 28 were tested for their fragrance strength and duration using the procedures described in Example 29 above. Specifically, each LLD sample contained a 2× concentrated LLD base (99.9 wt %) and a fragrance (0.1 wt %) or a blend (0.1 wt %) containing a fragrance (90 wt % of the total weight of the fragrance and Formula 28) and Formula 28 (10 wt % of the total weight of the fragrance and Formula 28). The following four fragrances were used: (a) 10-undecen-1-al, (b) n-dodecanal, (c) (4aR,5R,7aS,9R)-octahydro-2,2,5,8,8,9a-hexamethyl-4H-4-a,9-methanozuleno[5,6-d]-1,3-dioxole, and (4) tricyclo(5.2.1.02,6)dec-3-enyl acetate. Fragrances (a), (b), and (c) were added to the LLD samples as a 10 wt % solution in dipropylene glycol.

The results are summarized in FIGS. 6(A)-6(D). As shown in these figures, the samples containing Formula 28 exhibited superior fragrance strength and duration compared to the samples without Formula 28.

Example 33: Evaluation of Formula 28 in a Hard Surface Cleaning Solution

Sample Preparation

Hard surface cleaning solutions containing a fragrance with and without Formula 28 were tested for their fragrance strength and duration. Specifically, sample A (which contained Formula 28) was prepared as follows: Formula 28 (10 g; 25 wt %) and 2,6-dimethylhept-5-enal (30 g; 75 wt %) was mixed and stirred until homogenous to form a bullet.

The bullet thus formed (40 g; 62.5 wt %) was then mixed with an accompanying fragrance mixture "Fruity Floral" (24 g; 37.5 wt %) (Robertet Inc., Oakland, N.J.) to form a blend (64 g). 0.3 wt % of the blend thus formed was then added into a hard surface cleaner base. After the mixture was allowed to stand for 24 hours, it was transferred to a spray bottle to form sample A. Sample B (which contained no Formula 28) was prepared as follows: 55.6 wt % of 2,6-dimethylhept-5-enal was then mixed with 44.4 wt % of Fruity Floral (24 g; 37.5 wt %) to form a blend. 0.25 wt % of the blend thus formed was then added into a hard surface cleaner base. After the mixture was allowed to stand for 24 hours, it was transferred to a spray bottle to form sample B.

Evaluation Method

Two pieces of aluminum foil with a size of 10 inch squares were cut out from a large aluminum foil. A clean 8×8 inch ceramic tile was placed on top of each foil. Sample A (0.5 g) was sprayed onto one of the two foils by holding the spray bottle 6 inches away foil and spraying sample A onto the tile. Sample B (0.5 g) was sprayed on the other foil using the same method. The samples were allowed to sit uncovered for 1 hour and then were evaluated for their fragrance strength (i.e., at day 0). After this initial evaluation, the samples were left uncovered in a fragrance free room and were re-evaluated for their fragrance strength after 24 hours (i.e., at day 1).

Results

The results of the above evaluations were summarized in Table 3 below. As shown in Table 3, sample A (which contained Formula 28) unexpectedly exhibited superior fragrance strength compared to sample B (which contained no Formula 28) one day after they were applied to a hard surface.

TABLE 3

0.5 g of fragranced hard surface cleaner applied to tile and air dried for 1 hour before testing

| Day Evaluated After Application | Fragrance Strength of Sample A | Fragrance Strength of Sample B |
| --- | --- | --- |
| 0 | 4.3 | 4.3 |
| 1 | 2.4 | 1.8 |

Other embodiments are within the scope of the following claims.

What is claimed is:
1. A grafting composition, comprising:
a fragrance;
a coupling agent;
a polymerizable prepolymer which is a polymerizable monomer or oligomer selected from the group consisting of: acrylonitrile, sodium vinyl sulfonate, an ester, an alkylpyrrolidone, a carbodiimide, or a mixture thereof;
a graft initiator;
a catalyst; and at least one of
terpene or benzyl benzoate
wherein the coupling agent is a silane of formula (I):

in which $R_1$ is $C_1$-$C_{10}$ alkyl or $C_2$-$C_{10}$ alkenyl, and each of $R_2$, $R_3$, and $R_4$, independently, is $C_1$-$C_{10}$ alkyl, $C_1$-$C_{10}$ alkoxy, or $C_6$-$C_{30}$ aryl and the composition comprises from 0.1 ppm to 5000 ppm of the coupling agent.

2. The grafting composition of claim 1, wherein $R_1$ is vinyl and each of $R_2$, $R_3$, and $R_4$ is methoxy.

3. The grafting composition of claim 1, wherein the composition comprises from 2 wt % to 50 wt % of the prepolymer.

4. The grafting composition of claim 1, wherein the graft initiator comprises a salt of Ag, Fe, Co, or Cu, or a mixture thereof.

5. The grafting composition of claim 4, wherein the graft initiator consists of silver perchlorate.

6. The grafting composition of claim 1, wherein the composition comprises from 0.01 ppm to 10 ppm of the graft initiator.

7. The grafting composition of claim 1, wherein the catalyst comprises a peroxide, a peracid, a perbenzoate, a metabisulfite, a persulfate, or a mixture thereof.

8. The grafting composition of claim 7, wherein the catalyst consists of urea peroxide.

9. The grafting composition of claim 1, wherein the composition comprises from 0.01 ppm to 10 ppm of the catalyst.

10. The grafting composition of claim 1, further comprising a surfactant.

11. The grafting composition of claim 1, wherein the composition comprises from 1 wt % to 80 wt % of the fragrance.

12. The grafting composition of claim 1, wherein the composition comprises from 10 wt % to 80 wt % of a solvent.

13. The grafting composition of claim 1, wherein the composition comprises from 1 wt % to 80 wt % of the fragrance, from 2 wt % to 50 wt % of the prepolymer, from 0.01 ppm to 10 ppm of the graft initiator, and from 0.01 ppm to 10 ppm of the catalyst.

14. The grafting composition of claim 1, wherein the composition comprises from 1 wt % to 80 wt % of the fragrance, from 2 wt % to 50 wt % of the prepolymer, from 0.01 ppm to 10 ppm of the graft initiator, from 0.01 ppm to 10 ppm of the catalyst, from 0.01 wt % to 0.5 wt % of the surfactant, and from 10 wt % to 80 wt % of the solvent.

15. The grafting composition of claim 1, wherein:
the graft initiator consists of silver perchlorate, and,
the catalyst consists of urea peroxide.

16. The grafting composition of claim 1, wherein the prepolymer is a resin.

17. A grafting composition, comprising:
a fragrance;
a coupling agent;
a rosin ester;
silver perchlorate;
urea peroxide; and at least one of
terpene or benzyl benzoate;
wherein the coupling agent is a silane of formula (I):

$$Si-R_1R_2R_3R_4 \qquad (I),$$

in which $R_1$ is $C_1$-$C_{10}$ alkyl or $C_2$-$C_{10}$ alkenyl, and
each of $R_2$, $R_3$, and $R_4$, independently, is $C_1$-$C_{10}$ alkyl, $C_1$-$C_{10}$ alkoxy, or $C_6$-$C_{30}$ aryl and the composition comprises from 0.1 ppm to 5000 ppm of the coupling agent.

18. A grafting composition according to claim 17, comprising a polybutylene prepolymer.

19. A grafting composition according to claim 17, comprising vinyltrimethoxy silane.

20. A grafting composition according to claim 17, comprising beta-(3,4-epoxycyclohexylethyltriethoxysilane).

21. A grafting composition comprising a fragrance, an isobutylene/butylene copolymer, a hydrogenated rosin ester, benzyl benzoate, a terpene, a mineral oil, a non-ionic surfactant, trimethoxyvinylsilane, a polyalkylene glycol, an organomodified polydimethylsiloxane, urea peroxide, and silver perchlorate.

22. A consumer product, comprising the composition of claim 1.

23. The product of claim 22, wherein the product is a detergent, a softener, a deodorant, a shampoo, a fabric refresher, a dryer sheet, or a surface cleaner.

24. A method of washing a cloth item, comprising:
applying a composition of claim 1 to the cloth item;
washing the cloth item.

25. The method of claim 24, further comprising drying the cloth item after the washing step.

26. An article, comprising the grafting composition of claim 1, wherein the composition forms a compound including a fragrance moiety bonded to a polymeric moiety and wherein the compound is bonded to the article.

27. The article of claim 26, wherein the fragrance moiety is covalently bonded to the polymeric moiety.

28. The article of claim 27, wherein the fragrance moiety is covalently bonded to the polymeric moiety through a silane moiety.

29. The article of claim 26, wherein the compound is covalently bonded to the surface.

30. The article of claim 29, wherein the compound is covalently bonded to the surface through a siloxane moiety.

31. The article of claim 26, wherein the article is a cloth item.

* * * * *